US010350354B2

(12) United States Patent
Yodfat et al.

(10) Patent No.: US 10,350,354 B2
(45) Date of Patent: Jul. 16, 2019

(54) DEVICE AND METHOD FOR PREVENTING HYPOGLICEMIA

(75) Inventors: Ofer Yodfat, Maccabim-Reut (IL); Gali Shapira, Haifa (IL); Neesha Ramchandani, New York, NY (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1657 days.

(21) Appl. No.: 12/143,611

(22) Filed: Jun. 20, 2008

(65) Prior Publication Data

US 2009/0030398 A1    Jan. 29, 2009

Related U.S. Application Data

(60) Provisional application No. 60/959,191, filed on Jul. 11, 2007, provisional application No. 60/959,812, (Continued)

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14248* (2013.01); *G06F 19/3456* (2013.01);
(Continued)

(58) Field of Classification Search
CPC ........ A61M 5/1723; A61M 2202/0486; A61M 2230/201; A61M 5/14248;
(Continued)

(56) References Cited

U.S. PATENT DOCUMENTS

| 6,554,798 B1 * | 4/2003 | Mann ................ A61M 5/14244 |
| | | 604/131 |
| 2007/0078314 A1 | 4/2007 | Grounsell et al. ............ 600/319 |

(Continued)

FOREIGN PATENT DOCUMENTS

| EP | 1 281 351 A2 | 2/2003 | |
| EP | 1281351 A2 * | 2/2003 | ......... A61B 5/14532 |

OTHER PUBLICATIONS

Allen et al., "Nocturnal hypoglycemia: clinical manifestations and therapeutic strategies toward prevention", *Endocrine Practice*, 9(6):530-543 (2003).

(Continued)

*Primary Examiner* — Shefali D Patel
(74) *Attorney, Agent, or Firm* — Dinsmore & Shohl LLP

(57) ABSTRACT

A device and a method for prevention of hypoglycemia are disclosed. In one aspect, the device and the method for prevention of hypoglycemia can comprise receiving a target blood glucose (TBG) level corresponding to a desired level of glucose in a patient's body during a fasting time period; receiving a bedtime blood glucose (BBG) level corresponding to a level of glucose in the patient's body substantially at a beginning of the fasting time period (e.g. before bedtime); receiving a first set of parameters corresponding to a medical state of the patient; determining a therapeutic course of action based on the levels of the TBG, BBG and the medical state of the patent; and administering the therapeutic course of action to the patient.

25 Claims, 12 Drawing Sheets

Related U.S. Application Data filed on Jul. 16, 2007, provisional application No. 60/936,810, filed on Jun. 21, 2007.

(51) Int. Cl.
*G06F 19/00* (2018.01)
*G16H 50/50* (2018.01)

(52) U.S. Cl.
CPC .............. *A61M 2005/14208* (2013.01); *A61M 2005/14268* (2013.01); *A61M 2005/1726* (2013.01); *A61M 2205/3569* (2013.01); *A61M 2205/50* (2013.01); *A61M 2205/52* (2013.01); *A61M 2230/201* (2013.01); *G16H 50/50* (2018.01)

(58) Field of Classification Search
CPC ......... A61M 2005/14208; A61M 2005/14268; A61M 2005/1726; A61M 2205/3569; A61M 2205/50; A61M 2205/52; A61M 2230/005
USPC ...... 604/131, 151, 500, 503, 504, 65, 66, 67
See application file for complete search history.

(56) References Cited

U.S. PATENT DOCUMENTS

| | | | |
|---|---|---|---|
| 2007/0118405 A1 | 5/2007 | Campbell et al. ................. | 705/2 |
| 2007/0124002 A1 | 5/2007 | Estes et al. ...................... | 700/20 |
| 2007/0191702 A1 | 8/2007 | Yodfat et al. | |
| 2008/0172031 A1* | 7/2008 | Blomquist .......... | G06F 19/3468 604/500 |
| 2008/0215035 A1 | 9/2008 | Yodfat et al. | |

OTHER PUBLICATIONS

Anonymous: "Deltec Cozmo—Personalized Insulin Pump—Starting Guide", pp. 1-80 (2004).

The Diabetes Control and Complications Trial (DCCT) Research Group, "The Effect of Intensive Treatment of Diabetes on the Development and Progression of Long-Term Complications in Insulin-Dependent Diabetes Mellitus", N Engl J Med 329: 977-986 (1993).

The Diabetes Control and Complications Trial/Epidemiology of Diabetes Interventions and Complications (DCCT/EDIC) Study Research Group, "Intensive Diabetes Treatment and Cardiovascular Disease in Patients with Type 1 Diabetes", N Eng J. Med 353: 2643-53 (2005).

UK Prospective Diabetes Study (UKPDS) Group, Intensive Blood-Glucose Control with Sulphonylureas or Insulin Compared with Conventional Treatment and Risk of Complications in Patients with Type 2 Diabetes (UKPDS 33), The Lancet 352: 837-853 (1998).

UK Prospective Diabetes Study (UKPDS) Group, "Tight Blood Pressure Control and Risk of Macrovascular and Microvascular in Type 2 Diabetes: UKPDS 38", BMJ 317, (7160): 703-13 (1998).

Allen et al., "Nocturnal Hypoglycemia: Clinical Manifestations and Therapeutic toward Prevention", Endocrine Practice, 9(6): 530-543 (2003) (PMID: 14715482).

Perriello et al., "The Effect of Asymptomatic Nocturnal Hypoglycemia on Gylcemic Control in Diabetes Mellitus", N.E.J. Med., 319: 1233-1239 (1988) (PMID: 3054544).

Schiffrin et al., "Predicting nocturnal hypoglycemia ni patients with type 1 diabetes treated with continuous subcutaneous insulin infusion", Am. J. Med., 82(6): 1127-1132 (1987) (PMID: 3605131).

\* cited by examiner

EXAMPLES OF FOODS AND THEIR GI

| CLASSIFICATION | GI RANGE | EXAMPLES |
|---|---|---|
| LOW GI | 55 OR LESS | MOST FRUIT AND VEGETABLES (BUT NOT POTATO), OATS, BUCKWHEAT, WHOLE BARLEY, ALL-BRAN |
| MEDIUM GI | 56 – 69 | SUCROSE, BASMATI RICE |
| HIGH GI | 70 OR MORE | CORN FLAKES, BAKED POTATO, JASMINE RICE, WHITE BREAD, WHITE RICE, MARS BAR |

DEVICE AND METHOD FOR PREVENTING HYPOGLICEMIA

RELATED APPLICATIONS

This application claims the benefit of U.S. Provisional Application No. 60/936,810, filed on Jun. 21, 2007. This application also claims the benefit of U.S. Provisional Application No. 60/959,191, filed on Jul. 11, 2007. This application also claims the benefit of U.S. Provisional Application No. 60/959,812, filed Jul. 16, 2007.

FIELD OF THE INVENTION

A device and a method for sustained medical infusion of fluids are described. Some aspects of the device and the method relate to a portable insulin infusion device and a method for preventing hypoglycemia. Some aspects relate to an insulin dispensing patch that can monitor bodily glucose levels and a method for preventing hypoglycemia, during a fasting time period, including, for example, a nocturnal time period.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels, maintaining near constant glucose levels in the body.

Much of the burden of the disease to the user and to health care resources is due to the long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbAlc). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia by frequent glucose measurements and adjustment of insulin delivery is of utmost importance.

Frequent insulin administration can be done by multiple daily injections (MDI) with syringe or by continuous subcutaneous insulin injection (CSII) with insulin pumps. In recent years, ambulatory portable insulin infusion pumps have emerged as a superior alternative to multiple daily injections of insulin. These pumps, which deliver insulin at a continuous basal rate as well as in bolus volumes, were developed to liberate patients from repeated self-administered injections, and allow greater flexibility in dose administration.

Insulin pumps can deliver rapid acting insulin 24 hours a day, for example, through a catheter placed under the skin. The total daily insulin dose can be divided into basal and bolus doses. Basal insulin can be delivered continuously over 24 hours, and can keep the blood glucose levels in normal, desirable range between meals, overnight and during fasting time periods. Diurnal basal rates can be pre-programmed or manually changed according to various daily activities. Insulin bolus doses can be delivered before or after meals to counteract carbohydrates loads or during episodes of high blood glucose concentration levels. For example, the amount of insulin in the administered bolus can depends on several parameters corresponding to a medical state of the patient:

Amount of carbohydrates (Carbs) to be consumed, alternatively defined as "servings", wherein 1 serving=15 grams of Carbs.

Carbohydrate-to-insulin ratio (CIR), i.e. the amount of carbohydrates balanced by one unit of insulin which is measured in grams per one unit of insulin.

Insulin sensitivity (IS), i.e. the amount of blood glucose lowered by one unit of insulin.

Current blood glucose levels (CBG)

Target blood glucose levels (TBG), i.e. the desired blood glucose levels. TBG for most people with diabetes is in the range of 80-120 mg/dL before a meal, and less than 180 mg/dL 1-2 hours after the beginning of a meal.

Residual insulin (RI), i.e. the amount of stored insulin remained in the body after recent bolus delivery that is still active. This parameter is relevant when there is a short time interval between consecutive bolus doses (e.g. less than 5 hours).

Although the long term complications of the disease are mainly attributed to hyperglycemic states, hypoglycemia can also pose a major barrier in achieving glycemic targets. For example, it has been shown that asymptomatic nocturnal hypoglycemia can cause clinically important deterioration in glycemic control in patients receiving intensive insulin therapy by causing the Somogyi phenomenon. The Somogyi phenomenon is hyperglycemia induced by a counter-regulatory hormonal response to hypoglycemia (NEJM 1988; 319: 1233-1239.).

Nocturnal hypoglycemia, due to nocturnal hyperinsulinemia, is common in patients with type 1 diabetes and is usually asymptomatic. Nocturnal hyperinsulinemia can occur as a result of the insulin therapy. Although blood glucose levels can often be low during sleep, they are seldom measured routinely. Almost 50% of all episodes of severe hypoglycemia occurs at night during sleep. Such episodes can cause convulsions and coma and have been implicated as a precipitating factor in cardiac arrhythmias resulting in sudden death. Nocturnal hypoglycemia seems to have no immediate detrimental effect on cognitive function; however, on the following day, mood and well-being may be adversely affected. Recurrent exposure to nocturnal hypoglycemia may impair cognitive function; other substantial long-term morbidity includes the development of acquired hypoglycemia syndromes, such as impaired awareness of hypoglycemia (End Practice 2003; 9 (6):530-543).

The risk of hypoglycemia is enhanced by hypoglycemia unawareness and defective glucose counter regulation (e.g. impaired glucagon and attenuated adrenaline responses); conditions that are characteristic of diabetes associated neuropathy (specifically, autonomic sympathetic neuropathy). Hypoglycemia unawareness can occur when a person does not have the early symptoms of low blood glucose. As a result, the person cannot respond in the early stages, and severe signs of hypoglycemia, such as loss of consciousness or seizures, can be more likely.

The combination of hypoglycemia unawareness and defective glucose counter regulation is known as "hypoglycemia associated autonomic failure" (HAAF). A vicious cycle is created since symptomatic hypoglycemia itself reduces sympathetic adrenal response (i.e. adrenaline secretion), which subsequently further increases the unawareness of the succeeding hypoglycemic episode.

It can be concluded that prevention of hypoglycemic episodes, specifically nocturnal hypoglycemic episodes (hereinafter known altogether as "hypoglycemia"), is of utmost importance.

Currently, the strategies used by patients with diabetes for prevention of nocturnal hypoglycemic episodes are inaccurate and based on patient intuition—ingestion of a snack immediately prior to nocturnal sleep (or a fasting time period) containing an arbitrary amount of carbohydrates if blood glucose is low or administration of somewhat smaller amounts of insulin for the night. If the blood glucose is too high, the patient may administer a correction bolus of approximately suitable magnitude.

In view of the foregoing, it would be desirable to provide a device for insulin infusion and a corresponding method to prevent hypoglycemia and achieve better glycemic control, especially during fasting time periods (e.g., overnight sleep).

SUMMARY OF THE INVENTION

A device and a method are provided that can be used for prevention of hypoglycemia. In some embodiments, the device and a method can dispense insulin. The device and a method can also monitor glucose concentration levels, dispense insulin, and employ a method for preventing hypoglycemia. For example, the device and a method can continuously monitor body glucose levels, simultaneously deliver insulin bolus doses into the body, and employ a method for preventing hypoglycemia. In some embodiments, the device can be miniature, discreet, economical for the user and highly cost effective.

In one aspect, a method for prevention of hypoglycemia can comprise receiving a target blood glucose (TBG) level corresponding to a desired level of glucose in a patient's body during a fasting time period; receiving a bedtime blood glucose (BBG) level corresponding to the level of glucose in the patient's body substantially at the beginning of the fasting time period; receiving a first set of parameters corresponding to a medical state of the patient; providing the levels of the TBG, BBG and the medical state of the patent to a therapeutic course of action determining means; and, providing means for administering the therapeutic course of action to the patient.

In one variation, the therapeutic course of action includes at least one of the advising the patient to consume a calculated amount of carbohydrates (CC), adjusting the patient's basal rate (BR), advising the patient to adjust the BR, administering a correction bolus (CB), advising the patient to administer the CB.

In one variation, the first set of parameters comprises at least one of the patient's insulin sensitivity (IS), the patient's carbohydrate to insulin ratio (CIR), and the patient's residual insulin (RI), such that the RI corresponds to the level of residual insulin in the patient's body substantially at the beginning of the fasting time period (also referred to as the "bedtime" time period). In some implementations, the "fasting time period" can correspond to any period of time a user spends without food consumption. The fasting time period can begin after the user consumes a meal. Alternatively, the fasting time period can begin at any point in time prior to the next meal consumption.

The term "bedtime" can refer to the point in time just prior to an individual sleeping as part of a circadian pattern (e.g., a nocturnal time period). The term "bedtime" can also refer to a time immediately prior to a fasting time period (e.g., a time period where calories are not ingested, where the user/patient is either awake or asleep), which can include daytime periods (such time periods lasting generally between 4-12 hours or more). Regarding nocturnal "sleeping" time periods, for the majority of people, this period of time is at night (but could be during the day), and generally lasts from 5-10 hours.

In one implementation, if a correction bolus is needed or if a decrease in basal insulin is required for optimal bedtime (e.g., a fasting time period) blood glucose measurement, the pump can automatically change the regimen without user interface.

In another implementation, if a correction bolus is needed or if a decrease in basal insulin is required for optimal bedtime (e.g., a fasting time period) blood glucose measurement, the user is notified and may accept or reject the recommended bolus and basal modifications.

According to some embodiments, the method may be applied during the daytime, especially when the user suffers from hypoglycemic unawareness. In some embodiments, the hypoglycemia prevention method can be implemented by an insulin infusion device. In some embodiments, the hypoglycemia prevention method can be implemented by a glucose monitoring device. In still other embodiments, the hypoglycemia prevention method can be implemented by a device which can deliver insulin and monitor glucose.

In some embodiments, the hypoglycemia prevention method can be implemented in an insulin infusion device comprising an insulin dispensing patch unit and a remote control unit, wherein a glucose sensing apparatus (e.g. glucometer) may be integrated in the remote control unit. In one such embodiment, the dispensing patch unit may be composed of two parts: a reusable part that contains all electronic and driving elements (i.e. relatively expensive elements) and a disposable part that contains insulin reservoir and other inexpensive elements.

In some embodiments, the glucose sensing apparatus (e.g. glucometer) may alternatively be integrated in the reusable part of the infusion patch unit of the device. In still other embodiments, the hypoglycemia prevention method can be implemented by the remote control unit of the insulin infusion device. The nocturnal hypoglycemia prevention method could also be implemented by the reusable part of the dispensing patch unit of the device.

In another embodiment, the hypoglycemia prevention method can be implemented by the dispensing patch unit that continuously monitors body glucose concentration levels and can simultaneously deliver insulin into the body. The dispensing patch unit may comprise a reusable part and a disposable part.

In some embodiments, the hypoglycemia prevention method can be implemented by the remote control unit of the device. The method could be implemented by the reusable part of dispensing patch unit of the device. The method could also be implemented by both the reusable part of the dispensing patch unit of the device and the remote control unit of the device.

The device can include a miniature skin adherable patch that can continuously dispense insulin, and that employs a method for preventing hypoglycemia can also be provided. The device can comprise a miniature skin adherable patch that can continuously dispense insulin, monitor body glucose concentration levels (e.g. blood glucose, ISF glucose), and employ a method for preventing hypoglycemia.

In some embodiments, an insulin patch unit can be provided that includes disposable and reusable parts. The reusable part may contain all relatively expensive components and the disposable part may contain inexpensive components, thus providing a low cost product for the user and a highly profitable product for the manufacturer. The insulin patch may employ a method for preventing hypoglycemia.

In some embodiments, a device can be provided that comprises insulin and a continuous glucose monitor patch unit comprising disposable and reusable parts. The reusable part can contain all relatively expensive components and the disposable part contains inexpensive components, thus providing a low cost product for the user and a highly profitable product for the manufacturer. The device may employ a method for preventing hypoglycemia.

Some embodiments provide a device that comprises an insulin infusion patch unit that can be remotely controlled. The insulin infusion patch unit can employ a method for preventing hypoglycemia. The device can also comprise insulin and a continuous glucose monitor patch unit that can be remotely controlled, and that employs a method for preventing hypoglycemia.

In some embodiments, an insulin infusion pump can also be provided. The insulin infusion pump can employ a method for preventing hypoglycemia during a fasting time period (e.g., a nocturnal time period). The method can take into consideration the bedtime blood glucose levels (e.g., blood glucose levels immediately prior to a fasting time period), the residual insulin at that time, and the user's target bedtime (e.g., fasting time period) glucose levels. Hypoglycemia may be prevented by manipulation of the basal insulin of the pump and/or consumption of a known amount of carbohydrates and/or administration of a correction bolus.

DETAILED DESCRIPTION

Figures 1, 2A:
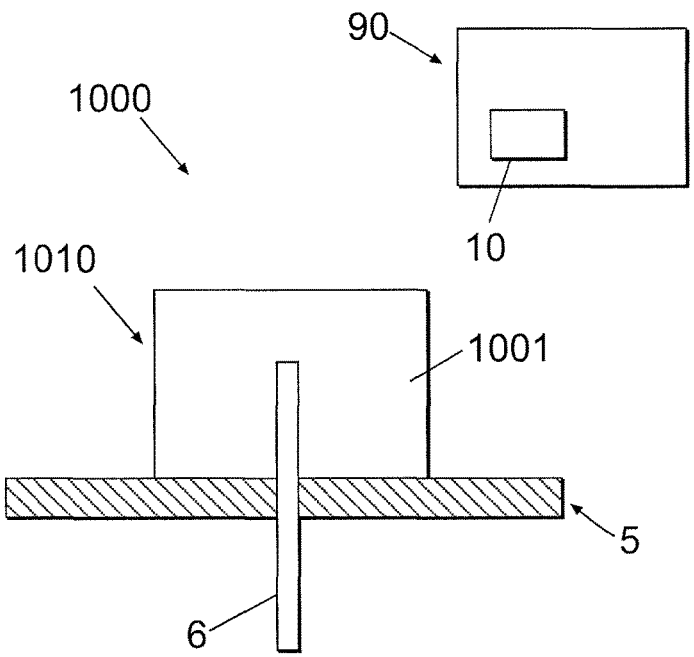
FIG. 1 provides a few examples of different foods and their corresponding GI.

A device and a method are provided that can be used for prevention of hypoglycemia. In some embodiments, the device can dispense insulin. The device and a method can also monitor glucose concentration levels, dispense insulin, and employ a method for preventing hypoglycemia. For example, the device can continuously monitor body glucose levels, simultaneously deliver insulin bolus doses into the body, and employ a method for preventing hypoglycemia.

In one aspect, a method for prevention of hypoglycemia can comprise receiving a target blood glucose (TBG) level corresponding to a desired level of glucose in a patient's body during a fasting time period; receiving a bedtime blood glucose (BBG) level corresponding to the level of glucose in the patient's body substantially at the beginning of the fasting time period; receiving a first set of parameters corresponding to a medical state of the patient; providing the levels of the TBG, BBG and the medical state of the patent to a therapeutic course of action determining means; and, providing means for administering the therapeutic course of action to the patient.

In one variation, the therapeutic course of action includes at least one of the advising the patient to consume a calculated amount of carbohydrates (CC), adjusting the patient's basal rate (BR), advising the patient to adjust the BR, administering a correction bolus (CB), advising the patient to administer the CB.

In one variation, the first set of parameters comprises at least one of the patient's insulin sensitivity (IS), the patient's carbohydrate to insulin ratio (CIR), and the patient's residual insulin (RI), such that the RI corresponds to the level of residual insulin in the patient's body substantially at the beginning of the fasting time period (also referred to as the "bedtime" time period).

In some variations, the hypoglycemia prevention can be conducted according to one or more of the following, performed in the order listed below or in any other suitable order:

1. The user or another party (e.g., nurse or physician) may set a target blood glucose (TBG) level (e.g. 120 mg/dL) for the user for the fasting time period. In some embodiments, this and/or other parameter(s) described herein may be preprogrammed into memory of the device (e.g., into read-only memory (ROM)).
2. The user may measure his/her bedtime blood glucose level (BBG) immediately prior (e.g., shortly before) to the fasting time period.
3. The residual insulin may be evaluated by the user or automatically by the device (presented on the remote control or pump screen).
4. The following calculations can be made:
    a. If the BBG is above TBG and there is no residual insulin in the body ("insulin on board") (i.e. BBG>TBG and no RI), a correction bolus should be administered. Calculating the correction bolus (CB) which is the amount of insulin needed to reach the target blood glucose (TBG) can be done as follows:

$$CB = (BBG - TBG)/IS$$

wherein CB=correction bolus, BBG=blood glucose prior to the fasting time period; TBG=target blood glucose, IS=insulin sensitivity.

b. If the BBG is above TBG and there is residual insulin (RI) in the body but the residual insulin is smaller than the correction bolus (i.e. BBG>TBG and RI<CB), a minimized correction bolus can be administered according to the following equation:

$$\boxed{(BBG - TBG)/IS - RI = CB_m}$$

wherein $CB_m$—minimized CB, RI—residual insulin.

If the BBG is lower than the TBG and there may be residual insulin in the body (i.e. BBG<TBG, RI≥0), or if the BBG is above TBG and there is residual insulin (RI) in the body and the residual insulin is larger than the correction bolus that would have been administered had there been no residual insulin (i.e. BBG>TBG and RI>CB had there been no RI), the user (also referred to as "patient") can be offered the following choices:

i. ingest a known amount of carbohydrates (hereinafter known as "correction carb" or CC) according to the following:

CC/CIR + (BBG-TBG)/IS + RI = 0

$$\boxed{CC = CIR*(RI + ((TBG-BBG)/IS))}$$

Wherein CIR—carbohydrate to insulin ratio ii. adjust (e.g. lower) his/her basal insulin for the fasting time period (since the basal rate is supposed to keep the blood glucose constant, lowering the basal rate for a defined time segment can raise the blood glucose to the desired level TBG).

iii. adjust (e.g. lower) his/her basal insulin for the fasting time period to a lesser extent than option ii and ingest a known amount of carbohydrates (less than the amount of option i).

In some implementations, a substantially constant basal rate, the magnitude and time of basal rate reduction, when BBG<TBG and RI≥0, or BBG>TBG and RI>CB had there been no RI, can be adjusted according to the following computations:

1. The time in which 1 unit of insulin is delivered is $t*basal=1\ U \to t=1/basal$ basal=[U/hour]
2. At time t the overall decrease in blood glucose is IS;
3. The residual insulin in the body will further lower the BG. The expected decrease in BG is marked as $BG_{ed}$, and agrees with the equation: $BG_{ed}=IS*RI$
4. Due to the low BBG, and the residual insulin in the body a new, temporal IS value (IS') can be defined as $IS'=IS-(TBG-(BBG-BG_{ed})$, as long as $IS>(TBG-(BBG-BG_{ed}))$
5. The basal rate can be modified (to basal') for the time segment $t=1/basal$ as follows: $IS'/basal'=IS/basal \to Basal'=(IS'/IS)*basal$
6. In case $IS<(TBG-(BBG-BG_{ed}))$, the time $t=1/basal$ is not sufficient since a negative basal rate can obviously not be administered. The time defined for the decreased rate is the time in which 2 units of insulin are delivered: $T*basal=2\ U \to T=2/basal$. At time T the overall decrease in blood glucose is 2IS.
$2IS'=2IS-(TBG-(BBG-BG_{ed})) \to IS'=(2IS-(TBG-(BBG-BG_{ed}))/2$
$2IS'/basal'=2IS/basal \to Basal'=(IS'/IS)*basal$
7. In case $2IS<(TBG-(BBG-BG_{ed}))$, the time T should be defined as the time in which 3 units of insulin are delivered, i.e. 3IS, and so on.

According to the above-noted embodiment, the basal rate can be modified by other calculations that reduce the rate by a different magnitude for different time segments. In the embodiment described above, the magnitude of basal rate reduction can be in accordance with a time segment that will provide 1 single unit of insulin. A longer or shorter time segment may be chosen to dictate the magnitude of basal rate reduction. The time segment $t=n/basal$ (n can be any number) can be used for the modified basal insulin rate. The basal insulin rate is $Basal'=(IS'/IS)*basal$ wherein $IS'=IS-((TBG-BBG)/n)$.

In some implementations, inconstant (variable) basal profiles can also be adjusted in order to prevent hypoglycemia. For example, the inconstant basal rate, the magnitude and time of basal rate reduction, when BBG<TBG and RI≥0, or BBG>TBG and RI>CB had there been no RI can be adjusted according to the following computations, performed in any suitable order:

1. $n_1=t_1*basal\ (c_1)$
   a. $t_1$—the time in which the basal rate is constant, i.e. a "time segment"
   b. $basal(c_1)$—the constant basal rate of the first time segment
   c. $n_1$—the amount of insulin (in units) that are administered in time $t_1$
2. $n_1IS'_1=n_1IS-\Delta-BG_{ed}$
   a. $n_1IS$—the overall decrease in BG over time segment $t_1$.
   b. $\Delta=TBG-BBG$;
   c. $BG_{ed}=IS*RI$
3. $IS'_1=IS-\Delta/n_1-BG_{ed}/n_1$ > If $IS'_1 > 0$, the basal rate of the first segment (only) should be modified according to equation 4

4. $Basal'_1=(IS'_1/IS)*basal$
5. If the time segment ($t_1$) is longer than a predefined T (e.g. T=3 hours), than the modification can be limited to time "T" according to the following:
   a. $n_1=T*basal\ (c_1)$
   b. $n_1IS'_1=n_1IS--\Delta-RI*IS$
   c. $IS'_1=IS-\Delta/n_1-RI*IS/n_1$
   d. If $IS'_1>0$ than $Basal'_1=(IS'_1/IS)*basal$ > If $IS'_1 < 0$, the next constant basal period or time segment, should be modified 6. $Basal'_1$=minimum ('min') basal rate (e.g. 0.025 U/h)
7. Instead of administering $n_1$ and decreasing the BG by $IS*n_1$, $(t_1*'min')$ U were administered and BG decreased by $IS*n_{min,t1}$ (wherein $n_{min\ t1}=t_1*'min'$)

8. $n_2 IS'_2 = n_2 IS - \Delta - RI*IS + IS*n_1 - IS*n_{min,t1}$, wherein $n_2 = t_2*basal$ ($c_2$)
9. $IS'_2 = IS - \Delta/n_2 - RI*IS/n_2 + IS*(n_1/n_2) - IS*(n_{min,t1}/n_2)$ > If $IS'_2 > 0$, the basal rate of the first segment should be changed to 'min' and the basal rate of the second segment should be modified according to equation 10

10. $Basal'_2 = (IS'_2/IS)*basal$

> If $IS'_2 < 0$, the next constant basal period should be modified

11. $Basal'_2 = $ 'min'
12. Instead of administering $n_2$ and decreasing the BG by $IS*n_2$, $(t_2*min)$ U were administered and BG decreased by $IS*n_{min,t2}$
13. $n_3 IS'_3 = n_3 IS - \Delta - RI*IS + IS*n_1 + IS*n_2 - IS*n_{mint1} - IS*n_{min,t2}$
14. $IS'_3 = IS - \Delta/n_3 - RI*IS/n_3 + IS*(n_1/n_3) + IS*(n_2/n_3) - IS*(n_{min,t1}/n_3) - IS*(n_{min,t2}/n_3)$
15. $Basal'_3 = (IS'_3/IS)*basal$ And so on.

Basal rate modification of an inconstant basal profile can generally be expressed according to the following:

For "y" being a time period in which the basal rate is constant:

$$IS'_y \bigg|_{y=1,2,3...} = IS - \frac{\Delta}{n_y} + \frac{\sum_{x=1}^{x=y-1} IS*n_x}{n_y} - \frac{\sum_{x=1}^{x=y-1} IS*n_{min,x}}{n_y} - \frac{BG_{ed}}{n_y}$$

Wherein $n_y = t_y * basal_y$

And $BG_{ed} = IS * RI$ $basal_y = \frac{IS'_y}{IS} * basal$

According to some embodiments, the user may lower his/her basal insulin for the fasting time period and ingest a known amount of carbohydrates. Combined carbohydrate consumption and basal rate reduction may be according to the following computations:

1. A $CC_x$ between 0 and $CC_{max}$ can be chosen, wherein $CC_{max}$ is the amount of carbohydrates recommended if a correction carb alone is applied, as described in 3-c-i.
2. The basal is reduced according to the selected $CC_x$ and the equations depicted in 4-c-ii—with the modification of the BBG parameter to $BBG' = BBG + (CC_x/CIR)*IS$ According to one embodiment, the fasting time period (e.g., nocturnal) target blood glucose value or zone (TBG) is somewhat higher than a normal (e.g., daytime) target blood glucose value or zone.

The bedtime TBG may optimally be set at 120 mg/dL (Am. J. Med. 1987 June: 82(6) 1127-32).

According to one embodiment, if a correction carb is recommended, a snack containing known amount of carbs of a high glycemic index (e.g. a marketed bag of pretzels) is preferable. The glycemic index (GI) is a ranking system for carbohydrates based on their effect on blood glucose levels in the first two hours. The snack should not be a high-fat or high protein food (which take longer to digest and are slower to affect BG). FIG. 1 shows a few examples of foods and their GI.

Figure 2B:
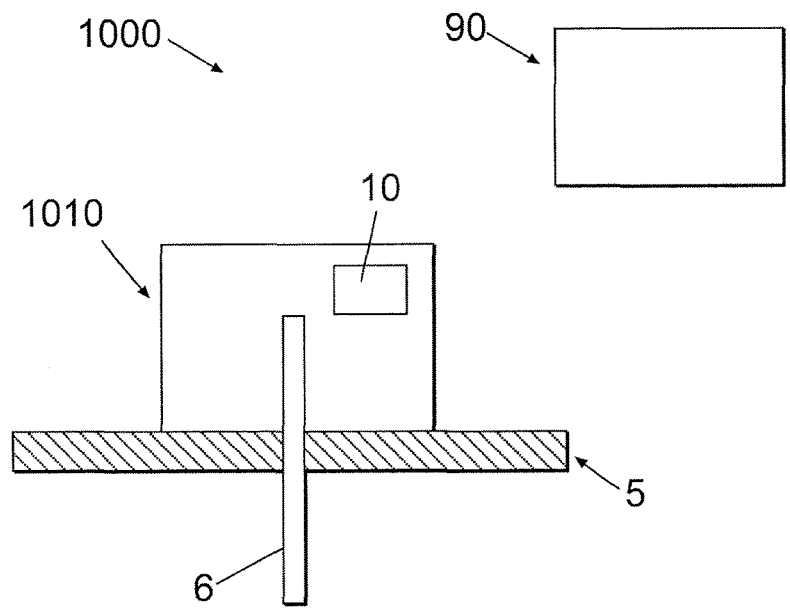
FIGS. 2 a-b illustrate one implementation of a device comprising an insulin infusion pump unit, a glucose measurement unit, and a hypoglycemia prevention feature.

FIGS. 2a-b show a device (1000) comprising an insulin infusion pump unit (1010), a glucose measurement unit (e.g. glucometer) (90), and a hypoglycemia prevention feature (10). Feature 10 may include any suitable hardware, software, or combination thereof. The insulin infusion pump unit (1010) may comprise a cannula (6) that penetrates the skin (5) to allow delivery of insulin.

In FIG. 2(a), the hypoglycemia prevention feature (10) is located in the glucose measurement unit (90). In FIG. 2(b), the hypoglycemia prevention feature (10) is located in the insulin infusion pump unit (1010).

According to one embodiment (not shown), the insulin infusion pump communicates with a remote control unit allowing programming, user inputs and data acquisition. The hypoglycemia prevention feature may be installed in the remote control unit.

According to another embodiment, the insulin infusion pump contains a glucometer. The glucometer may be installed in the remote control unit of the pump or in the pump unit itself. The hypoglycemia prevention feature may be located in the glucometer, pump unit, or remote control unit.

According to another embodiment, the system comprises an insulin infusion pump, a continuous glucose measurement (CGM) unit, and a hypoglycemia prevention feature. The hypoglycemia prevention feature may be located in either the pump unit or the CGM unit.

According to another embodiment, the insulin infusion pump unit comprises a continuous glucose measurement (CGM) means. The infusion pump and continuous glucose measurement (CGM) means are in the same housing and may communicate with a remote control unit. A hypoglycemia prevention feature may be located in the CGM and pump unit, or in the remote control unit.

Figure 3:
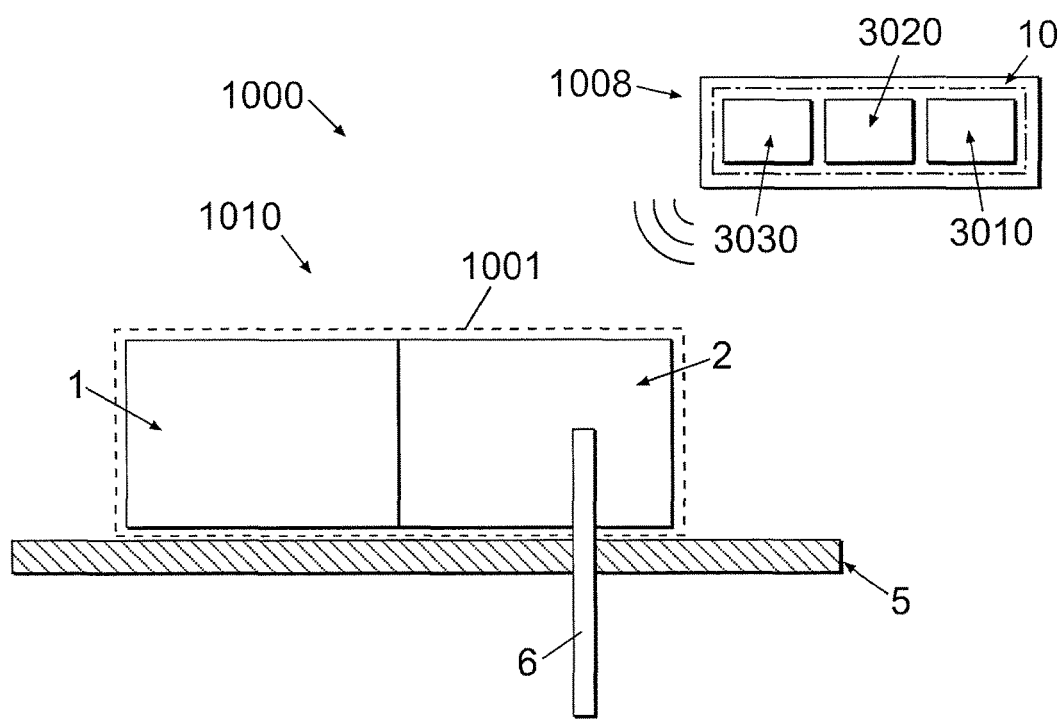
FIG. 3 shows one implementation of the insulin infusion device comprising an insulin dispensing unit and a remote control unit that contains a hypoglycemia prevention feature.

FIG. 3 shows an insulin infusion device (1000) comprising of a patch unit (1010), which can be adhered to the user's skin (5), and a remote control unit (1008), which communicates with the patch unit (1010), allowing programming, user inputs and data acquisition.

Manual inputs can be carried out by buttons (not shown) located on the patch unit (1010). The patch unit (1010) can be composed of one housing (1001) or two housings comprising reusable (1) and disposable (2) parts.

The patch unit (1010) can comprise a cannula (6) that penetrates the skin (5) to allow delivery of insulin. The patch unit (1010) can be directly attached to the user's skin by adhesive means (not shown) or can be attached to a dedicated cradle unit (not shown) that is adherable to the user's skin (5) and allows connection and disconnection of the patch unit (1010) as described in the patent application U.S. Ser. No. 60/876,679 herein incorporated by reference in its entirety.

In accordance with the invention, the remote control unit (1008) may contain the hypoglycemia prevention feature (10) which requires a processor (3010), input means (3020) and display (3030). The input means are required for the hypoglycemia prevention feature (10) and for patch unit (1010) programming. The control unit (1008) may contain additional indication means e.g. audible, vibrational, etc.

Figure 4A:
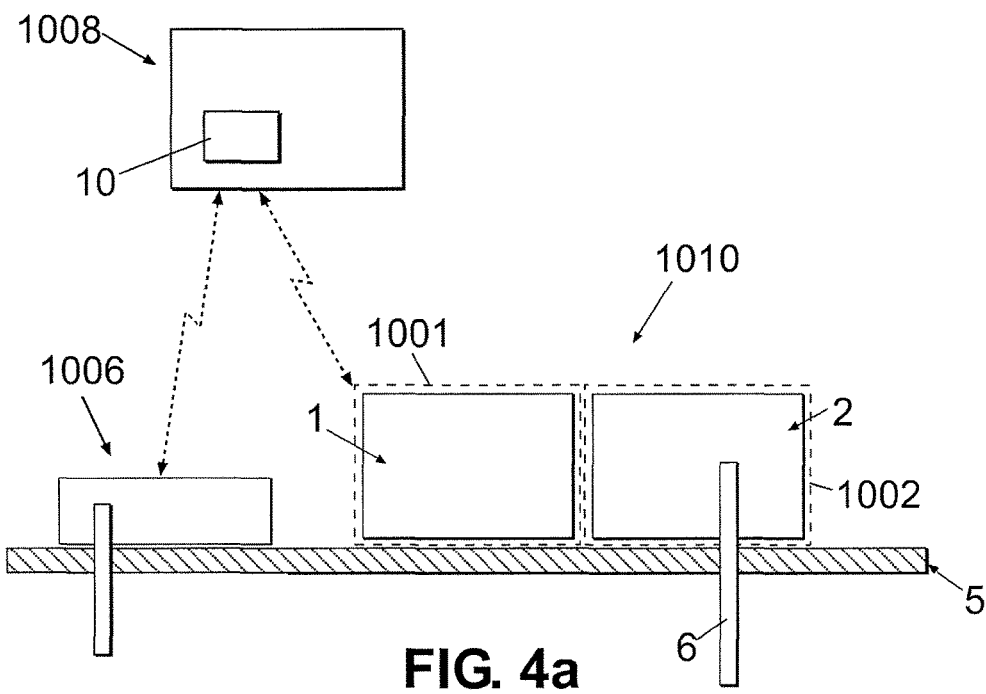
FIGS. 4 a-b show some implementations of the insulin infusion device containing various continuous subcutaneous glucose monitors for providing blood glucose readings (BG).
Figure 4B:
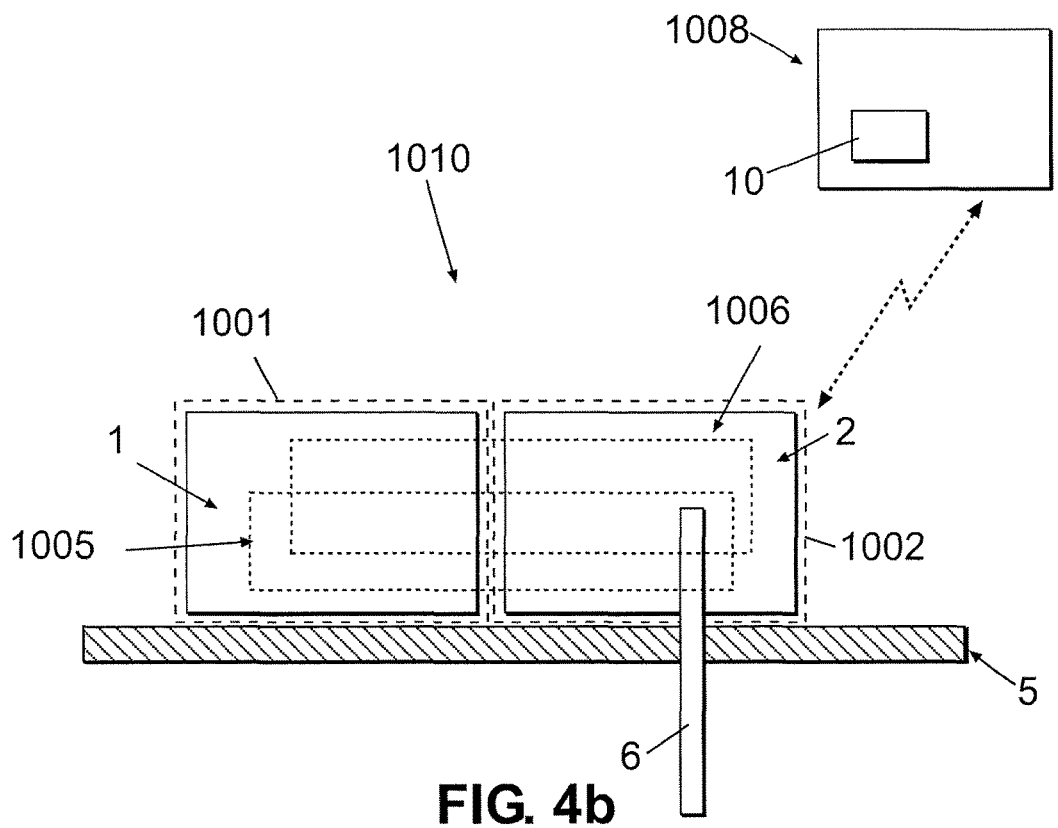

FIGS. 4a-b show another preferred embodiment of the invention in which blood glucose readings, needed for the hypoglycemia prevention feature (10) can be received from a continuous subcutaneous glucose monitor (1006). A communication channel between the continuous subcutaneous glucose monitor (1006) and the hypoglycemia prevention feature (10) residing in the remote control unit (1008) is maintained, allowing programming, data handling, and user inputs.

FIG. 4a shows an embodiment in which the current blood glucose (BG) is measured by an independent continuous subcutaneous glucose monitor (1006).

FIG. 4b shows an embodiment in which the continuous subcutaneous glucose sensing (monitoring) apparatus (1006) is integrated within the patch unit (1010) of the insulin delivery device.

The insulin dispensing apparatus (1005) and glucose sensing apparatus (1006) constitute a single delivery device, and may use a single cannula (6) for both dispensing and sensing as described in detail in our previous U.S. application Ser. No. 11/706,606 (herein incorporated by reference in its entirety).

In some implementations (not shown), the sensing apparatus and the dispensing apparatus have separate cannulae that penetrate the skin (5) and reside in the subcutaneous tissue. The delivery device of this embodiment may be comprised of two parts—a reusable part (1) and a disposable part (2), each part has corresponding housing (1001, 1002).

Figure 5:
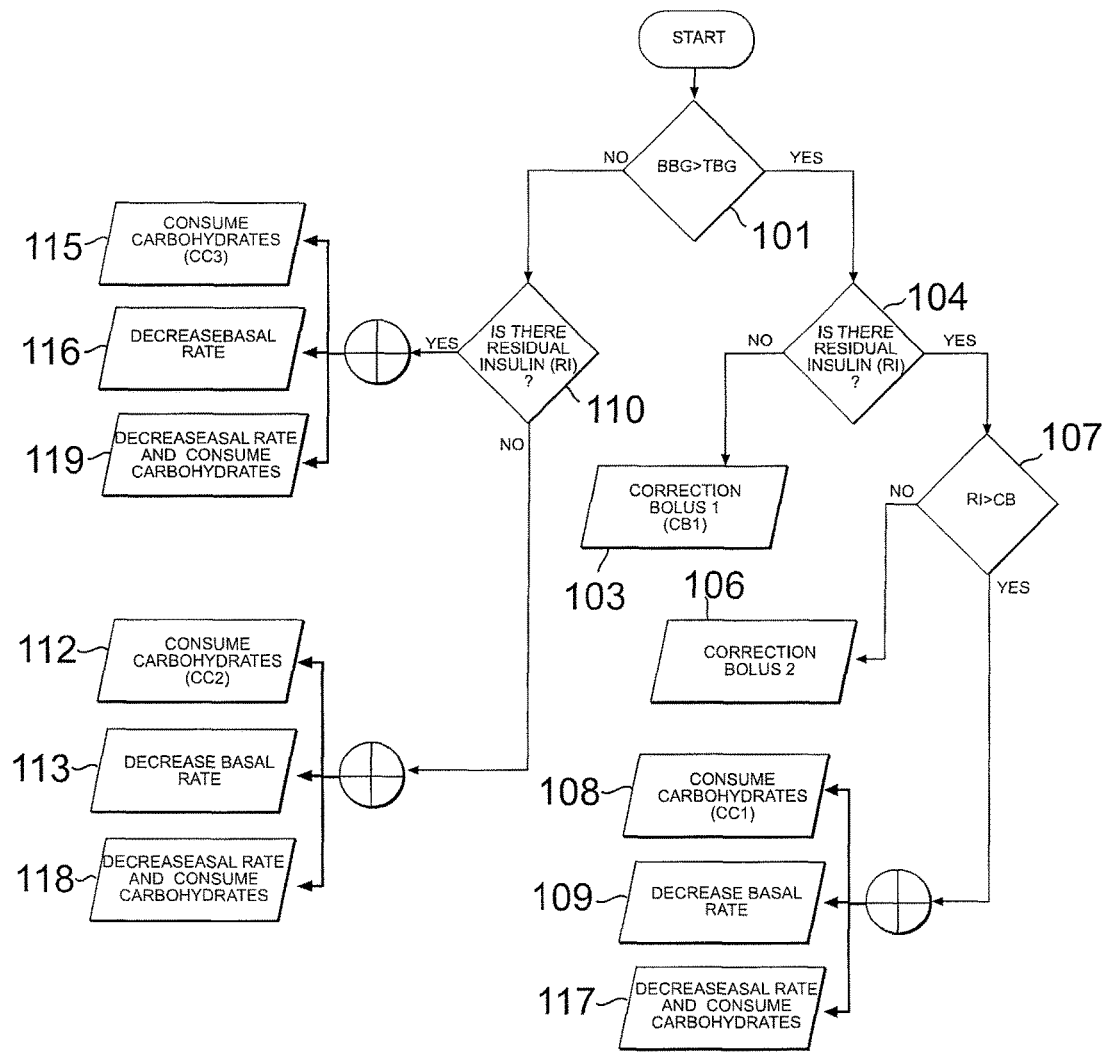
FIG. 5 shows a block diagram representing some aspects of the algorithm that can be utilized by the hypoglycemia prevention method.

FIG. 5 shows a block diagram representing some aspects of the algorithm that can be utilized by the hypoglycemia prevention method. For example, the measured bedtime (e.g., time prior to a fasting time period) blood glucose (BBG) is compared with the target blood glucose (TBG), see numeral (101). If the BBG is higher than the target blood glucose (TBG) (e.g. 120 mg/dL), the residual insulin is quantified, see numeral (104). If there is no residual insulin (RI) in the body from previous boluses, than a correction bolus dose (CB1) should be administered, see numeral (103). The correction bolus is as follows:

CB1=(BBG−TBG)/IS

Wherein CB1—correction bolus, BBG—blood glucose at bedtime (e.g., prior to or substantially at the beginning of a fasting time period), TBG—target blood glucose, IS—insulin sensitivity.

If the measured blood glucose (BBG) at bedtime is higher than the target blood glucose (TBG) but there is residual insulin (RI) in the body from previous boluses, than the RI is compared with the correction bolus that would have been given had there been no residual insulin at all (i.e. CB1), see numeral (107). Two options are then evaluated:

If the residual insulin is smaller than the correction bolus that would have been given had there been no residual insulin at all (i.e. CB1), a smaller correction bolus should be administered (CB2), see numeral (106). The correction bolus is as follows: CB2=(BBG−TBG)/IS−RI, wherein RI—residual insulin.

If the residual insulin is larger than the correction bolus that would have been given had there been no residual insulin at all (i.e. CB1), three further options are applicable:
The user ingests carbohydrates to raise the blood glucose levels, see numeral (108). The amount of carbs to be consumed are according to the following equation: CC1=CIR*(RI+((TBG−BBG)/IS))
wherein CC1—correction carbohydrate
The basal rate for the night/fasting time period is modified, see numeral (109).
The basal rate can be modified along with carbohydrate consumption, see numeral 117.

For a substantially constant nocturnal basal rate profile, the following modifications in the basal rate can be performed to prevent hypoglycemia:
Due to the residual insulin in the body a new, temporal IS value (IS') can be defined as IS'=IS−(TBG−(BBG−$BG_{ed}$)), wherein $BG_{ed}$=RI*IS. The basal rate may modified (to basal') for the time segment t=1/basal as follows: Basal'=(IS'/IS)*basal
In case IS<(TBG−(BBG−$BG_{ed}$)), the time t=1/basal is not sufficient since a negative basal rate can obviously not be administered. The time defined for the decreased rate may be prolonged to the time in which 2 units of insulin are delivered: T*basal=2 U→T=2/basal. At time T the overall decrease in blood glucose is 2IS. 2IS'=2IS−(TBG−(BBG−$BG_{ed}$))→ IS'=(2IS−(TBG−(BBG−$BG_{ed}$))/2 and Basal'=(IS'/IS) *basal
In case 2IS<(TBG−(BBG−$BG_{ed}$)), the time T may be defined as the time in which 3 units of insulin are delivered, i.e. 3IS, and so on.

For an inconstant nocturnal basal rate profile, the following modifications in the basal rate can be performed.
Due to the residual insulin in the body a new, temporal IS value (IS') can be defined as:

$$IS'_y \Big|_{y=1,2,3\ldots} = IS - \frac{\Delta}{n_y} + \frac{\sum_{x=1}^{x=y-1} IS * n_x}{n_y} - \frac{\sum_{x=1}^{x=y-1} IS * n_{min,x}}{n_y} - \frac{BG_{ed}}{n_y}$$

For "y" being a time period in which the basal rate is constant:
Wherein:

Δ=TBG−BBG $n_y = t_y * basal_y$

And $BG_{ed} = IS * RI$ $basal_y = \frac{IS'_y}{IS} * basal$

Combined carbohydrate consumption and basal rate reduction, see numeral 117, may be performed according to the following computations:
A $CC_x$ between 0 and $CC_1$ is selected by the user (i.e. 0<$CC_x$<$CC_1$),
The basal rate is reduced according to the selected $CC_x$ and the equations depicted above for constant or inconstant basal rate, with the modification of the BBG parameter to BBG'=BBG+(CC$_x$/CIR)*IS If the measured blood glucose (BBG) at bedtime (e.g., prior to a fasting time period) is lower than the target blood glucose (TBG), than the RI is evaluated. see numeral (110). If there is no residual insulin (RI) in the body from previous boluses, than three options can be considered:

The user ingests carbohydrates to raise the blood glucose levels, see numeral (112). The amount of carbs to be consumed are according to the following equation:

CC2=(CIR*(TBG−BBG))/IS

The basal rate for the fasting time period is modified, see numeral (113).

The basal rate can be modified along with carbohydrate consumption, see numeral 118.

For a substantially constant nocturnal basal rate profile, the following modifications in the basal rate can be performed to prevent hypoglycemia:

Due to the low BBG, a new, temporal IS value (IS') can be defined as

IS'=IS−(TBG−BBG). The basal rate may be modified (to basal') for the time segment t=1/basal as follows:
Basal'=(IS'/IS)*basal In case IS<TBG−BBG, the time t=1/basal is not sufficient since a negative basal rate can obviously not be administered. The time defined for the decreased rate may be prolonged to the time in which 2 units of insulin are delivered: T*basal=2 U→T=2/basal. At time T the overall decrease in blood glucose is 2IS. 2IS'=2IS−(TBG−BBG))→IS'=(2IS−(TBG−BBG))/2 and Basal'=(IS'/IS)*basal In case 2IS<(TBG−BBG), the time T may be defined as the time in which 3 units of insulin are delivered, i.e. 3IS, and so on.

For an inconstant nocturnal basal rate profile, the following modifications in the basal rate can be performed:

Due to the low BBG, a new, temporal IS value (IS') can be determined as follows:

$$IS'_y \Big|_{y=1,2,3...} = IS - \frac{\Delta}{n_y} + \frac{\sum_{x=1}^{x=y-1} IS * n_x}{n_y} - \frac{\sum_{x=1}^{x=y-1} IS * n_{min,x}}{n_y}$$

For "y" being a time period in which the basal rate is constant
Wherein:

$\Delta$=TBG−BBG $n_y = t_y * basal_y$ $$basal_y = \frac{IS'_y}{IS} * basal$$

Combined carbohydrate consumption and basal rate reduction, see numeral 118, can be performed as detailed for numeral 117 with the exception that CCx<CC2 and not CC1.

If the measured blood glucose (BBG) at bedtime (e.g., prior to a fasting time period) is lower than the target blood glucose (TBG) but there is residual insulin (RI) in the body from previous boluses, than three options can be considered:

The user ingests carbohydrates to raise the blood glucose levels, see numeral (115). The amount of carbs to be consumed may be performed as detailed for numeral 108.

The basal rate for the night is modified, see numeral (116). Basal rate modifications, for a constant or inconstant basal profile, may be performed as detailed for numeral 109.

The basal rate can be modified along with carbohydrate consumption, see numeral 119. Basal rate modifications, for a constant or inconstant basal profile, combined with carbohydrate consumption, may be performed as detailed for numeral 117, with the exception that CCx<CC3 and not CC1.

Figure 6:
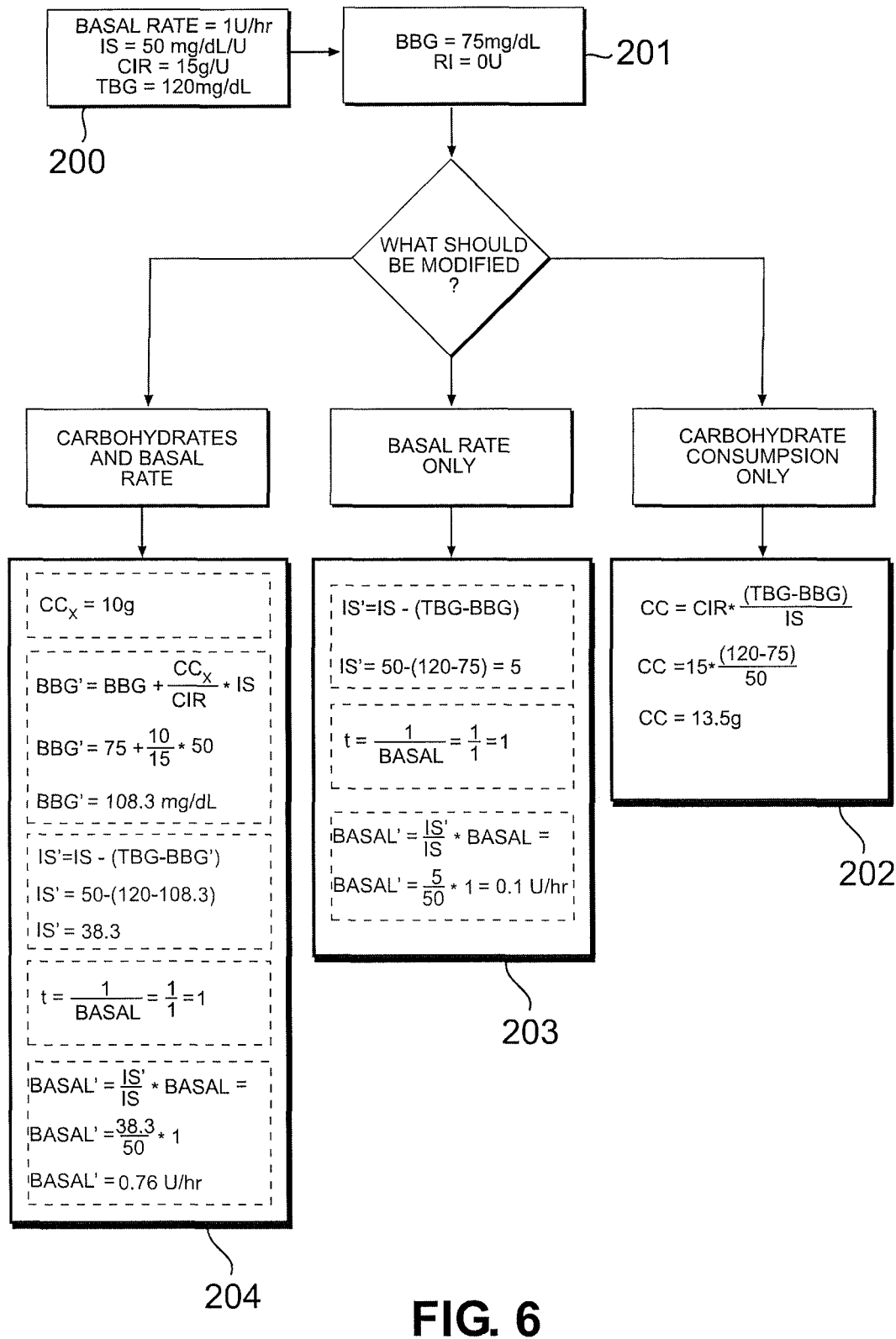
FIG. 6 shows a block diagram illustrating some aspects of one example of the hypoglycemia prevention method.

FIG. 6 shows a block diagram illustrating some aspects of one example of the hypoglycemia prevention method, in which the measured blood glucose at bedtime is lower than the target BG, there is no residual insulin left in the body from previous boluses (201), and the user's nocturnal basal profile comprises a constant basal rate (1 U/h).

The patient's constant basal rate, insulin sensitivity (IS), carbohydrate to insulin ratio (CIR) and target blood glucose (TBG) are known, see numeral (200). The patient may either consume a calculated amount of carbohydrates (202) (e.g. 13.5 grams of carbs are needed in the described example), change the basal rate (203), or change the basal rate and consume carbohydrates (204).

According to the embodiment the basal rate may be modified by numerous calculations that reduce the rate by a different magnitude for different time segments. In the given embodiment, the magnitude of basal rate reduction is in accordance with a time segment that will provide 1 single unit of insulin.

In the given example, the basal rate may be reduced to 0.1 U/h for one hour to prevent nocturnal hypoglycemia. In the given example, the user may consume carbohydrates in a smaller amount than calculated in numeral 202 (10 g in the example) and reduce the basal rate to a lesser extent than calculated in numeral 203 (0.76 U/h), see numeral 204.

Figure 7:
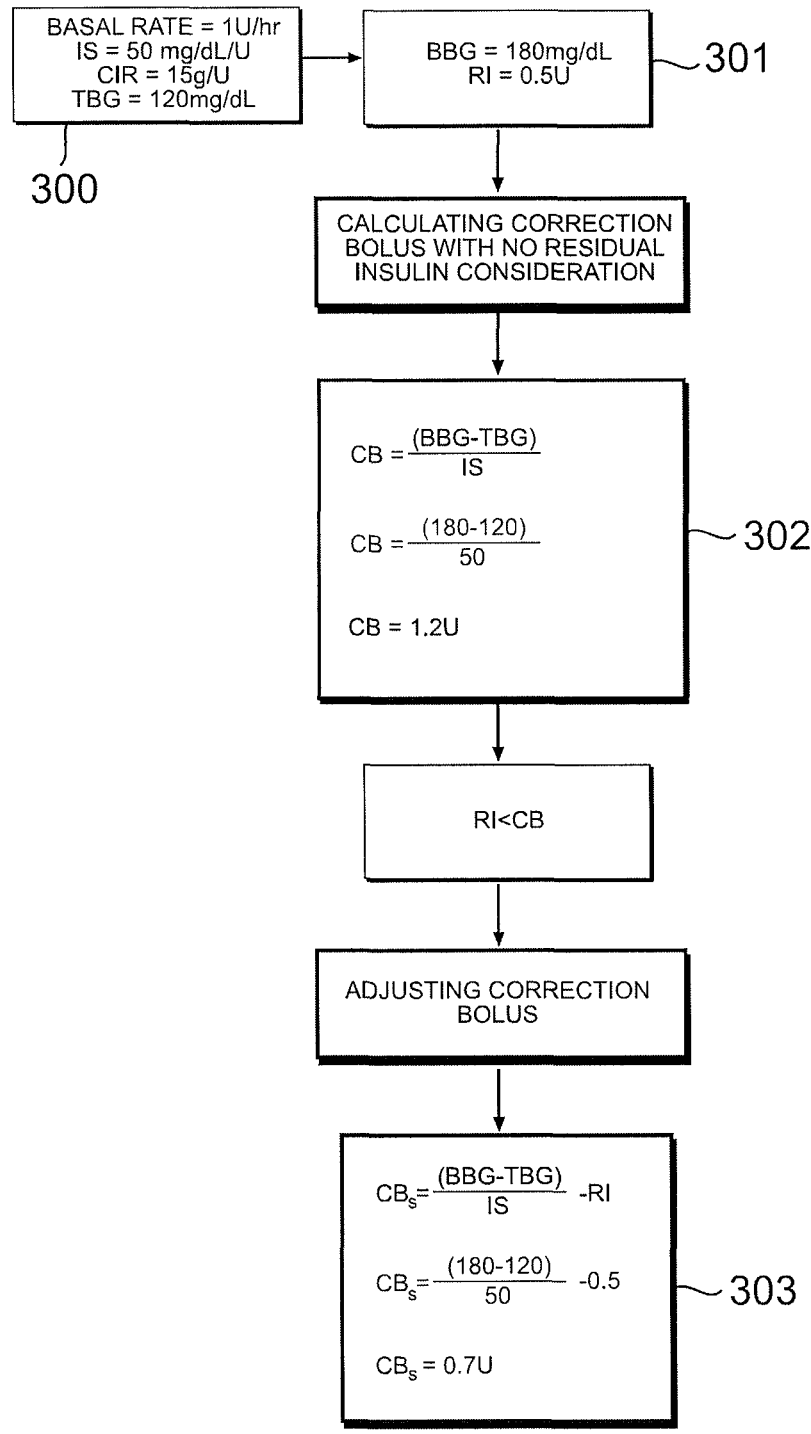
FIG. 7 shows a block diagram illustrating some aspects of another example of the hypoglycemia prevention method.

FIG. 7 shows a block diagram illustrating some aspects of another example of the hypoglycemia prevention method, in which the measured blood glucose at bedtime (e.g., prior to a fasting time period) is higher than the target BG and there is residual insulin left in the body from previous boluses (301).

The patient's constant basal rate, insulin sensitivity (IS), carbohydrate to insulin ratio (CIR) and target blood glucose (TBG) are known, see numeral (300). The correction factor can be calculated while avoiding the residual insulin, see numeral (302). Since the correction factor can be larger than the residual insulin (in the example: 0.5<1.2), than the patient is recommended to administer a smaller correction bolus (CBs) of insulin. The user should administer, according to the example, only 0.7 U of insulin instead of 1.2 U.

Figure 8A:
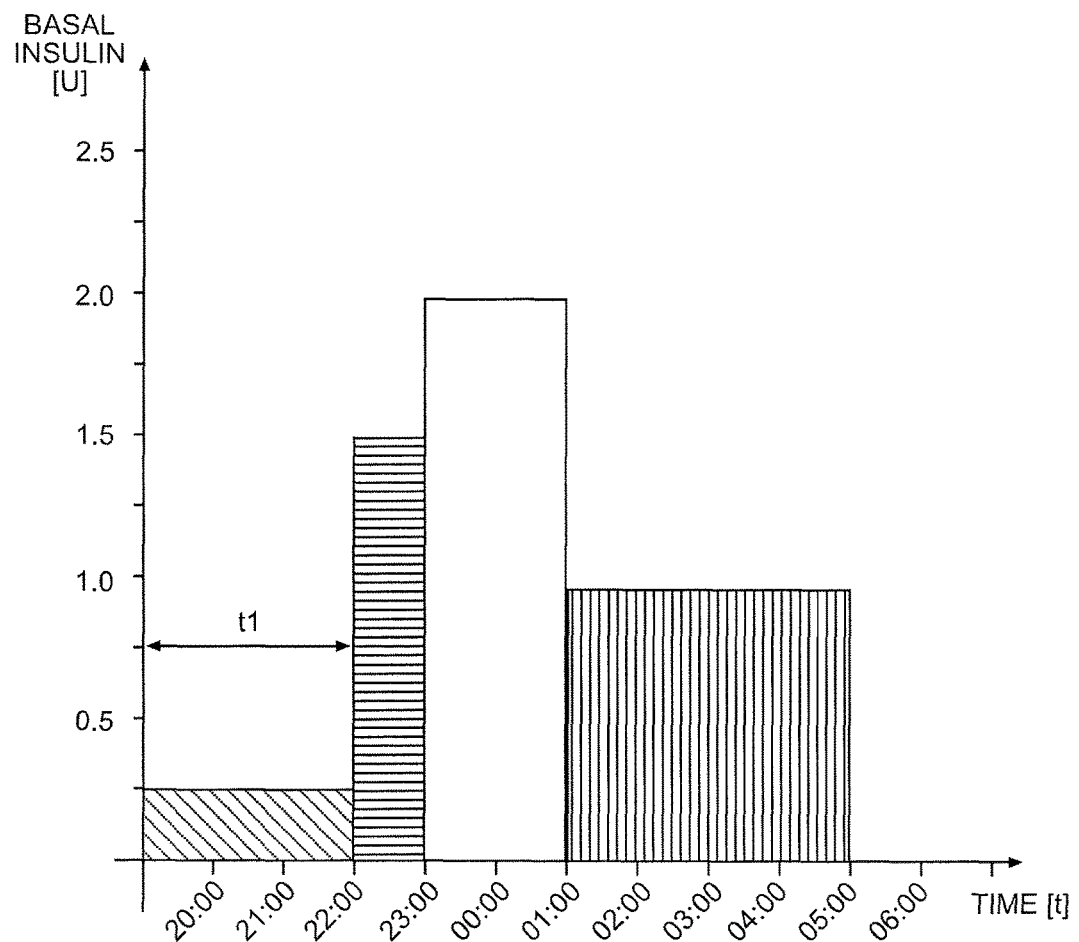
FIGS. 8 a-c illustrate some aspects of another example of the hypoglycemia prevention method.
Figure 8B:
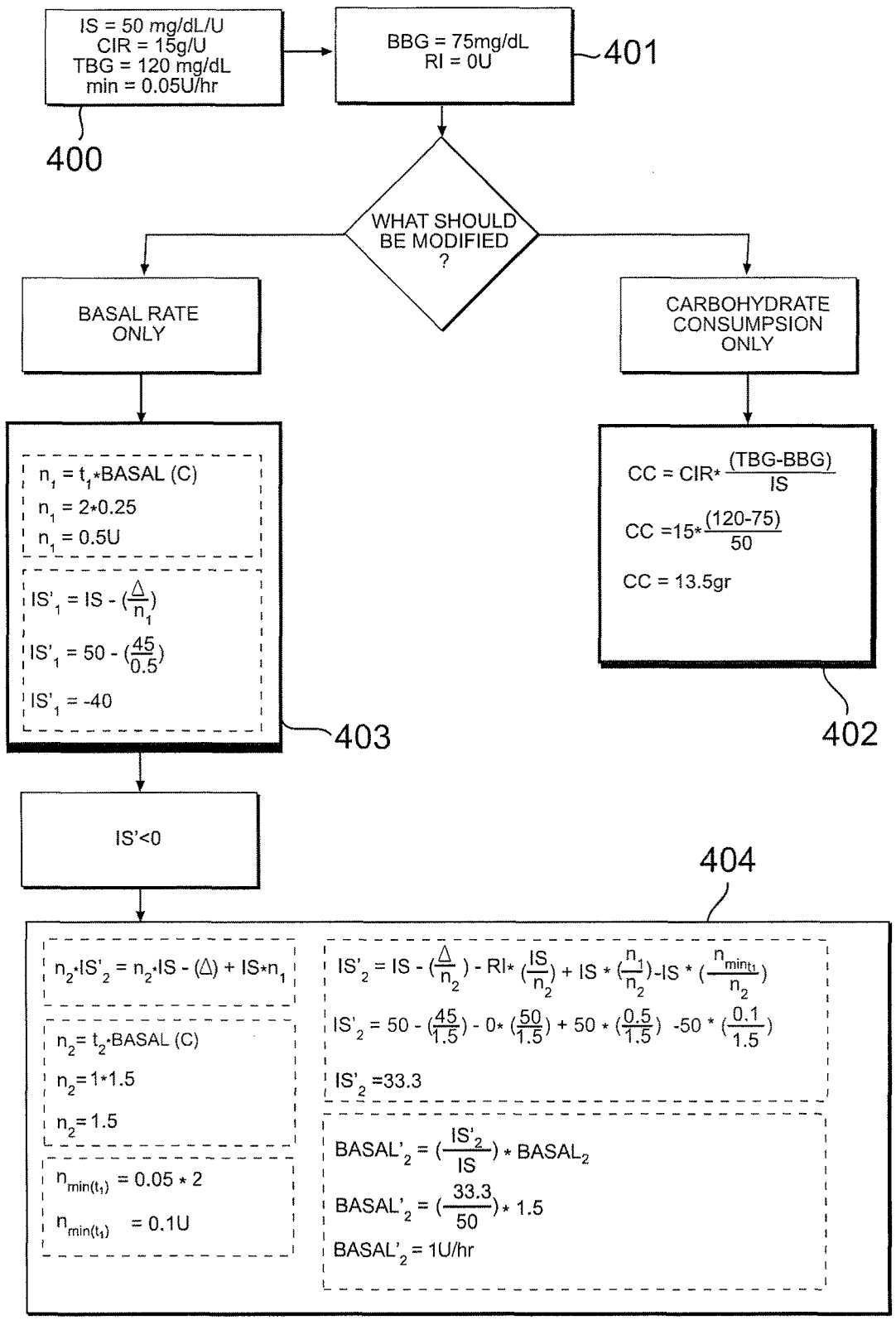

FIG. 8a shows an example of a graph representing an inconstant nocturnal basal insulin profile of a user. FIG. 8b shows a block diagram representing an example of the nocturnal hypoglycemia prevention method in which the measured blood glucose at bedtime (e.g., prior to a fasting time period) is lower than the target BG and there is no residual insulin left in the body from previous boluses (401).

The user's insulin sensitivity (IS), carbohydrate to insulin ratio (CIR) target blood glucose (TBG) and minimal possible basal rate ('min') are known, see numeral (400). The user may consume a calculated amount of carbohydrates (402), according to the following calculation: CC=(CIR*(TBG−BBG))/IS=(15*(120−75))/50=13.5 g.

In some implementations, the user can change the basal rate according to the following calculations, depicted in numerals 403 and 404:

1. $n_1 = t_1 * \text{basal} (c_1) = 2(h) * 0.25 \ (U/h) = 0.5 \ u$
2. $n_1 IS'_1 = n_1 IS - \Delta - RI * IS \rightarrow 0.5 * IS'_1 = 0.5 * 50 - 45 - 0 * 50 = -20$
   a. $n_1 IS$—the overall decrease in BG over time segment $t_1$.
   b. $\Delta = TBG - BBG = 120 - 75 = 45$
3. $IS'_1 = IS - \Delta/n_1 - RI * IS/n_1 = 50 - 45/0.5 - 0/0.5 = -40$ > $IS'_1 < 0$ so the next constant basal period, or time segment, should be modified, see numeral 204

4. $\text{Basal}'_1 = \text{'min'} = 0.05 \ U/h$
5. Instead of administering $n_1$ (i.e. 0.5 U) and decreasing the BG by $IS * n_1$ (i.e. $50 * 0.5 = 25$), $0.05 * 2 = 0.1$ U were administered, decreasing the BG by $IS * n_{min,t1}$ (i.e. $50 * 0.1 = 5$)
6. $n_2 IS'_2 = n_2 IS - \Delta - RI * IS + IS * n_1 - IS * n_{min,t1}$, wherein $n_2 = t_2 * \text{basal} (c_2) = 1 * 1.5 = 1.5$
7. $IS'_2 = IS - \Delta/n_2 - RI * IS/n_2 + IS * (n_1/n_2) - IS * (n_{min,t}/n_2) = 50 - 45/1.5 - 0/1.5 + 50 \ (0.5/1.5) - 50(0.1/1.5) = 33.3$
8. $\text{Basal}'_2 = (IS'2/IS) * \text{basal}_2 = (33.3/50) * 1.5 = 1 \ U/h$ The basal rate can be decreased to minimum (e.g. 0.05 U/h) in the first time segment (2 hours) and may be decreased to 1.0 U/h in the second time segment (1 h). In some implementations (not shown), the user may consume an amount of carbohydrates smaller than that calculated in (402), and decrease the basal rate accordingly. For example, the user may consume 10 g of carbs (<13.5) and decrease the basal rate according to the following calculation:

$BBG' = BBG + (CC_x/CIR) * IS = 75 + (10/15) * 50 = 108.3$
$\Delta = TBG - BBG' = 120 - 108.3 = 11.7$
$IS'_1 = IS - \Delta/n_1 - RI * IS/n_1 = 50 - 11.7/0.5 - 0/0.5 = 26.6$
$\text{Basal}'_1 = (IS'_1/IS) * \text{basal}_1 = (26.6/50) * 0.25 = 0.13 \ U/h$ All in all, the user consumed 10 g of carbs and decreased the basal rate from 0.25 U/h to 0.13 U/h for the first time segment (i.e. 2 hours).

Figure 8C:
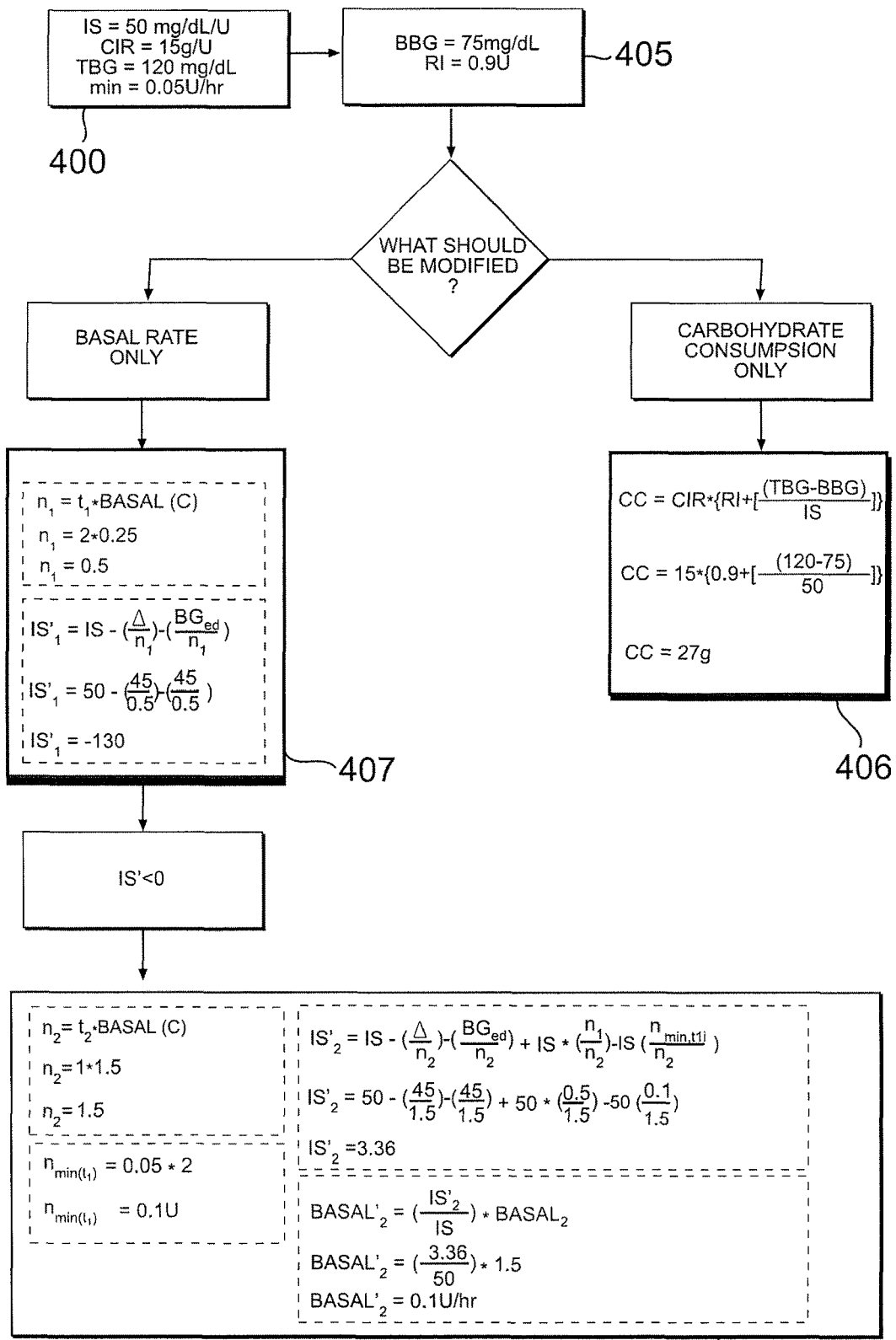

FIG. 8c shows a block diagram representing an example of the nocturnal carbohydrate prevention method in which the measured blood glucose at bedtime (e.g., prior to a fasting time period) is lower than the target BG and there is 0.9 units of residual insulin left in the body from previous boluses (405).

The user's minimal basal rate, insulin sensitivity (IS), carbohydrate to insulin ratio (CIR) and target blood glucose (TBG) are known, see numeral (400). The user may either consume a calculated amount of carbohydrates (406), according to the following calculation: $CC = (CIR * (RI + ((TBG - BBG)/IS)) = (15 * (0.9 + ((120 - 75)/50)) = 27 \ g$.

In some implementations, the user can change the basal rate according to the following calculations, as depicted in numerals 403 and 404:

1. $n_1 = t_1 * \text{basal} (c_1) = 2 * 0.25 = 0.5$
2. $n_1 IS'_1 = n_1 IS - \Delta - BG_{ed} = 0.5 * 50 - 45 - 50 * 0.9 = -65$
   a. $n_1 IS$—the overall decrease in BG overtime segment $t_1$.
   b. $\Delta = TBG - BBG$;
   c. $BG_{ed} = IS * RI$ 3. $IS'_1 = IS - \Delta/n_1 - BG_{ed}/n_1 = 50 - 45/0.5 - 45/0.5 = -130$ > $IS'_1 < 0$ so the next constant basal period, or time segment, should be modified, see numeral 408

4. $\text{Basal}'_1 = \text{'min'} = 0.05 \ U/h$
5. Instead of administering $n_1$ and decreasing the BG by $IS * n_1$ (i.e. 25 mg/dL), $0.05 * 2 = 0.1$ U were administered, decreasing the BG by $IS * n_{min,t1}$ (i.e. $50 * 0.1 = 5$ mg/dL)
6. $n_2 IS'_2 = n_2 IS - \Delta - BG_{ed} + IS * n_1$, wherein $n_2 = t_2 * \text{basal} (c_2) = 1.5 \ U$
7. $IS'_2 = IS - \Delta/n_2 - BG_{ed}/n_2 + IS * (n_1/n_2) - IS * (n_{min,t1}/n_2) = 50 - 45/1.5 - 45/1.5 + 50 \ (0.5/1.5) - 50(0.1/1.5) = 3.36$
8. $\text{Basal}'_2 = (IS'_2/IS) * \text{basal}_2 = (3.36/50) * 1.5 = 0.1 \ U/h$ The basal rate may be diminished to 'min' in the first time segments and may be reduced to 0.1 U/h in the second time segment.

Figure 9:
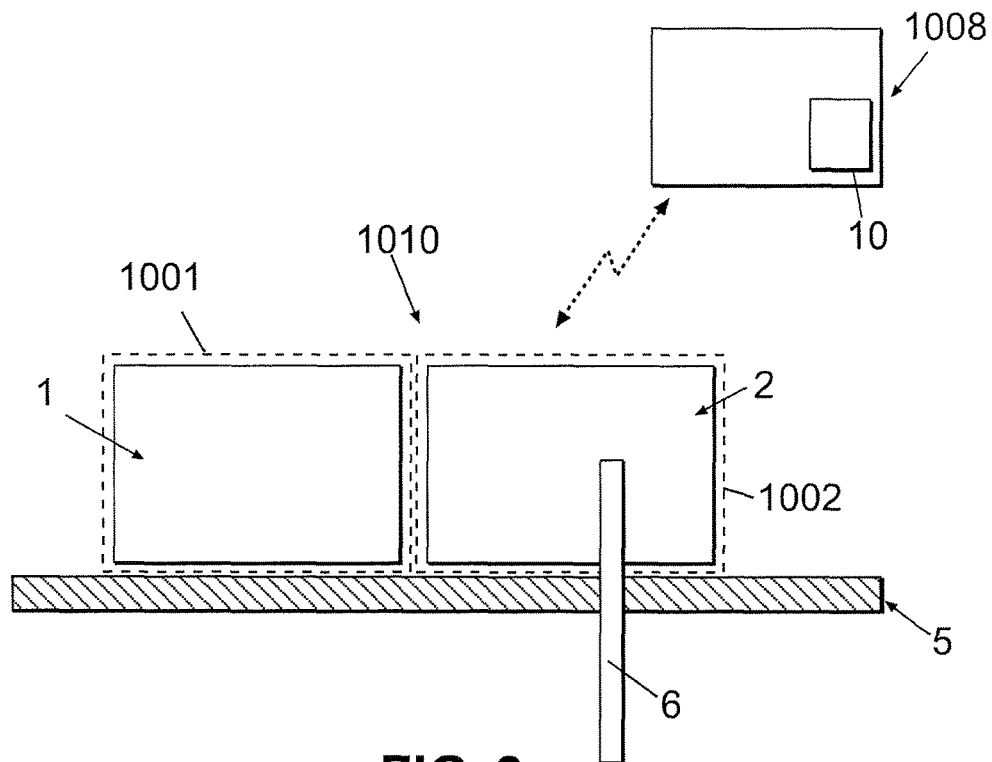
FIG. 9 is a schematic drawing of an exemplary insulin infusion device including a patch unit composed of a reusable part and a disposable part and a remote control unit that can contain some aspects of the hypoglycemia prevention feature.

FIG. 9 shows an embodiment of the insulin delivery device, wherein the patch unit (1010) is composed of two parts located in two housings (1001, 1002)—a reusable part (1) and a disposable part (2). The relatively cheap components of the device reside in the disposable part (2) (e.g. cannula (6)) and the relatively expensive components reside in the reusable part (1). In another preferred embodiment (not shown) the cannula (6) can be attached to a skin adhered cradle unit allowing the connection and disconnection of the patch unit to and from the cradle unit.

The device may comprise a remote control unit (1008) with an integrated hypoglycemia prevention feature (10). Programming can be carried out by the remote control or by buttons (not shown) located on the patch unit.

Figure 10A:
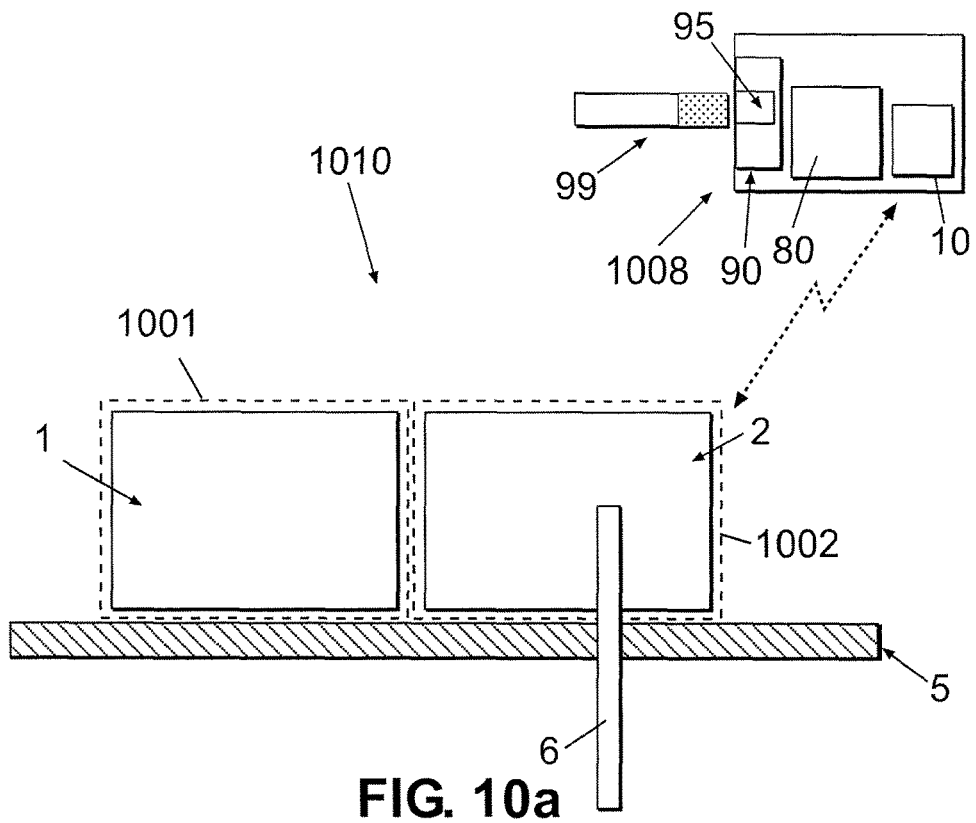
FIGS. 10 a-c show an exemplary insulin infusion device containing blood glucose monitor in three different locations providing blood glucose (BG) readings for some implementations of the hypoglycemia prevention feature.
Figure 10B:
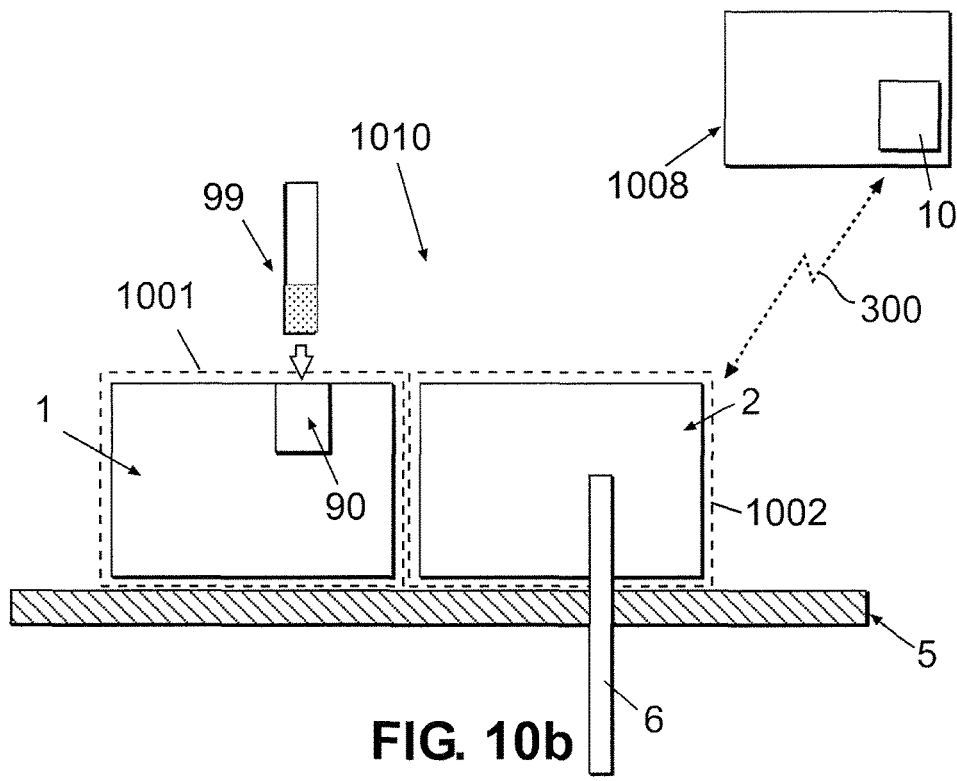
Figure 10C:
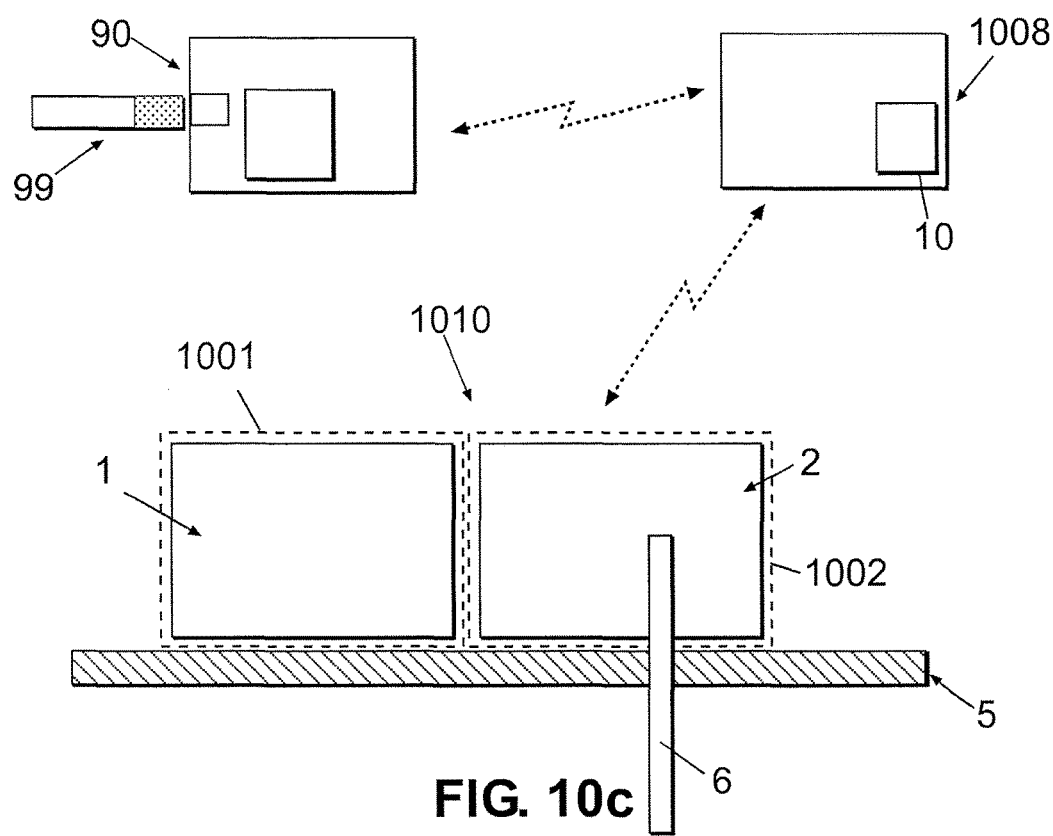

FIGS. 10a-c show three different embodiments of the device, each contains a glucometer (90) to be used as blood glucose (BG) inputs for the hypoglycemia prevention feature (10).

FIG. 10a shows a glucometer (90) located in the remote control unit (1008) of the device. The glucometer (90) comprises an opening (95) for receiving of a test strip (99). The user extracts blood from the body, places a blood drop on the test strip (99) and inserts the strip (99) into the opening (95). The glucose readings are displayed on a screen (80) of the remote control unit (1008).

FIG. 10b shows a glucometer (90) located in the reusable part (1) of the patch unit (1010). A communication channel (300) between the glucometer (90) residing in the patch unit (1010) and the nocturnal hypoglycemia prevention feature (10) residing in the remote control unit (1008) is maintained, allowing programming, data handling, and user inputs.

FIG. 10c shows an embodiment in which glucose readings are directly or remotely (90) received from an independent glucometer.

Figure 11A:
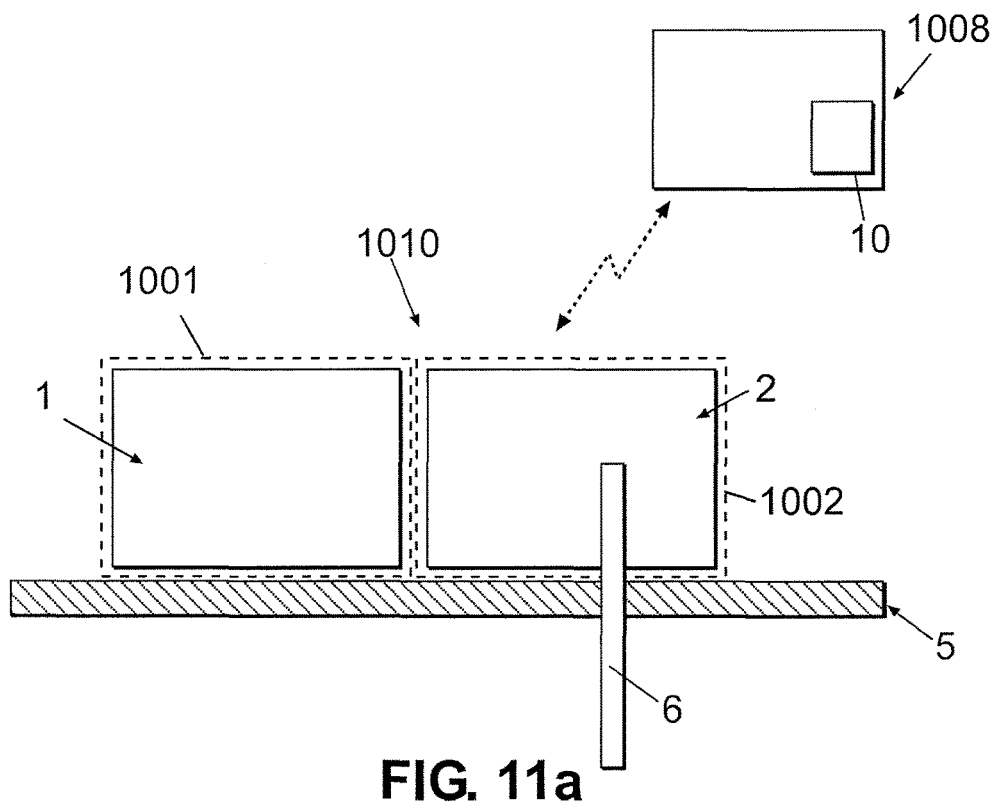
FIG. 11 a-b show two exemplary implementations for locating the hypoglycemia prevention feature.
Figure 11B:
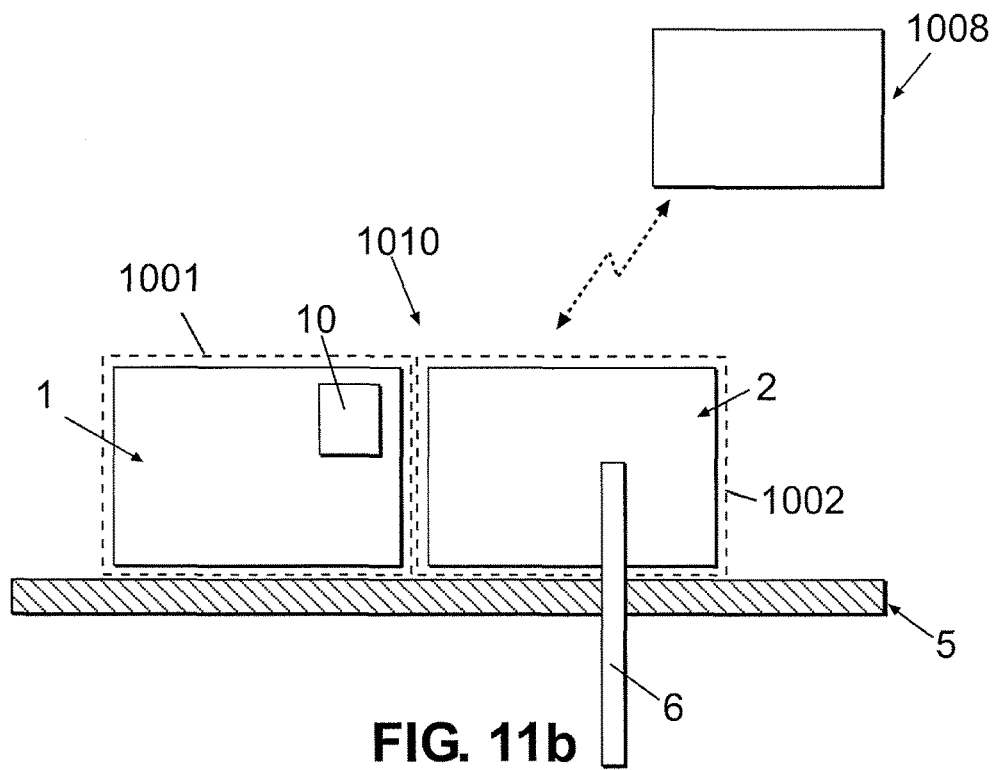

FIGS. 11a-b show two embodiments of the device with different locations of a hypoglycemia prevention feature (10). In FIG. 11a, the hypoglycemia prevention feature (10) is located in the remote control unit (1008). In FIG. 11b the hypoglycemia prevention (10) is located in the reusable part (1) of the patch unit (1010).

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein does not require the particular order shown, or sequential order, to achieve desirable results. Other implementations may be within the scope of the following claims.

Any and all patents, applications, articles and/or publications referenced in this specification are hereby incorporated by reference herein in their entireties.

Although illustrative embodiments of the invention have been described in detail herein with reference to the accompanying drawings, it is to be understood that the invention is not limited to those embodiments, and that various changes and modifications can be effected therein by one skilled in the art without departing from the scope and spirit of the invention.

What is claimed is:

1. A method for glycemic control to prevent hypoglycemia during a fasting time period, comprising:
   receiving a target blood glucose (TBG) level corresponding to a desired level of glucose in a patient's body during the fasting time period;
   receiving a beginning blood glucose (BBG) level corresponding to a measured glucose level in the patient's body substantially at a beginning of the fasting time period;
   receiving a first set of parameters comprising the patient's insulin sensitivity (IS), the patient's carbohydrate to insulin ratio (CIR), and the patient's residual insulin (RI), said RI corresponding to a level of residual insulin in the patient's body substantially at the beginning of the fasting time period;
   comparing the BBG level against the TBG level; and
   determining a therapeutic course of action including adjusting the patient's basal rate (BR) based on the levels of the TBG, the BBG and the first set of parameters wherein the therapeutic course of action includes:
   (a) advising the patient to consume a calculated amount of carbohydrates (CC), with the calculated amount of carbohydrates (CC) being calculated in the following ways:
      (i) $CC=CIR*(RI+((TBG-BBG)/IS))$ when BBG<TBG and the RI>0,
      (ii) $CC=(CIR*(TBG-BBG))/IS$ when BBG<TBG, and the RI is substantially negligible, and
      (iii) $CC=CIR*(RI+((TBG-BBG)/IS))$ when BBG>TBG and RI>(BBG-TBG)/IS, and
   (b) administering a correction bolus (CB) in the patient's body, based upon (i) the comparison of the BBG level against the TBG level and (ii) the determined therapeutic course of action, with the correction bolus (CB) being calculated in the following ways:
      (i) $CB=(BBG-TBG)/IS$ when BBG>TBG and there is substantially no RI, and
      (ii) $CB=(BBG-TBG)/IS-RI$ when BBG>TBG and (BBG-TBG)/IS >RI.

2. The method of claim 1, wherein the therapeutic course of action further includes allowing the patient to choose an amount of carbohydrates which is less than the calculated amount of carbohydrates (CC) and one of:
   adjusting the BR to a modified basal rate (BR'), and
   advising the patient to adjust the BR to the modified basal rate (BR').

3. The method of claim 2, further comprising adjusting the patient's basal rate (BR) for a time segment (t)=n/BR to the modified basal rate (BR') if the BBG level is less than the TBG level, the BR is substantially constant and the RI is substantially negligible, wherein the BR'=(IS'/IS)*BR, and IS'=IS-(TBG-BBG)/n, wherein IS' is a temporal IS value of the patient, and where n is a positive integer number.

4. The method of claim 2, further comprising adjusting the BR for a time segment (t)=n/BR to the modified basal rate (BR') if BBG<TBG and RI>0 and the patient's basal rate (BR) is substantially constant; wherein IS' is a temporal IS value of the patient, $BG_{ed}$ is an expected decrease in BG, and wherein: n is a positive number;
   $BR'=(IS'/IS)*BR$;
   $IS'=-((TBG-(BBG-BG_{ed})/n$; and,
   $BG_{ed}=IS*RI$.

5. The method of claim 2, further comprising adjusting the patient's basal rate (BR) to the modified basal rate (BR') upon determining that the BR is substantially inconstant.

6. The method of claim 2, further comprising adjusting the BR to the modified basal rate (BR') upon determining ((BBG<TBG and RI≥0) or (BBG>TBG and RI>CB)) and the patient's basal rate (BR) substantially changes over time, wherein $$IS'_y = IS - \frac{\Delta}{n_y} - \frac{BG_{ed}}{n_y} + \frac{\sum_{x=1}^{x=y-1} IS * n_x}{n_y} - \frac{\sum_{x=1}^{x=y-1} IS * n_{min \cdot x}}{n_y};$$

$$y = 1, 2, 3 \ldots$$

wherein:
$t_y$ is a period of time in which BR is substantially constant;
$t_x$ is another period of time;
n is a positive integer number;
$n_y$ is an amount of insulin (in units) that is administered during the period of time $t_y$;
$n_x$ is an amount of insulin (in units) that is administered during the period of time $t_x$;
$n_{min,x}$ is an amount of insulin (in units) that is administered during the period of time $t_x$ with a minimal possible basal rate;
IS is an overall decrease in blood glucose;
IS'y is a temporal IS value during the period of time $t_y$;
BG is a blood glucose;
BGed is an expected decrease in BG;
$BR_x$ is a basal rate during the period of time $t_x$;
BR' is the modified basal rate; and
wherein:

$$\Delta = TBG - BBG;$$

$$ny = ty * BR';$$

$$nx = tx * BRx;$$

$nmin, x = tx * BRmin$ (BRmin = minimal possible basal rate);

$$BGed = IS * RI, \text{ and}$$

$$BR' = \frac{IS'_y}{IS} * BR.$$

7. The method according to claim 6 wherein if a time segment ($t_1$) is longer than a predefined time segment (T), then the adjustment is limited to T according to the following:
a. $n_1 = T*BRc$, wherein BRc is a basal rate at a constant time segment;
b. $IS'_1 = IS - \Delta/n_1 - RI*IS/n_1$;
c. If $IS'_1 > 0$ then $BR'_1 = (IS'_1/IS)*BR$ for time segment (T);
wherein:
$n_1$ is an amount of insulin (in units) that is administered in the time segment $t_1$;
$IS'_1$ is an overall decrease in blood glucose in the time segment $t_1$; and
$BR'_1$ is a modified (adjusted) basal rate for the time segment $t_1$.

8. The method of claim 2, wherein the adjustment of the patient's basal rate is reducing the patient's basal rate.

9. The method of claim 1, wherein the fasting time period corresponds to a nocturnal time period.

10. A non-transitory computer readable medium comprising computer-executable instructions recorded thereon for performing the method of claim 1.

11. The method of claim 1, wherein the adjustment of the patient's basal rate is reducing the patient's basal rate.

12. A device for glycemic control to prevent hypoglycemia during a fasting time period, comprising:
a processor which receives:
a target blood glucose (TBG) level corresponding to a desired level of glucose in a patient's body during the fasting time period,
a beginning blood glucose (BBG) level corresponding to a measured level of glucose in the patient's body substantially at a beginning of the fasting time period,
a first set of parameters comprising the patient's insulin sensitivity (IS), the patient's carbohydrate to insulin ratio (CIR), and the patient's residual insulin (RI), said RI corresponding to a level of residual insulin in the patient's body substantially at the beginning of the fasting time period, and
wherein said processor:
compares the BBG level against the TBG level; and
determines a therapeutic course of action that includes an adjustment to the patient's basal rate (BR) based on the levels of the TBG, the BBG, and the first set of parameters, and
wherein the therapeutic course of action includes:
(a) advice to the patient to consume a calculated amount of carbohydrates (CC), with the calculated amount of carbohydrates (CC) calculated and advised by the processor in the following ways:
(i) CC=CIR*(RI+((TBG−BBG)/IS)) when BBG<TBG and the RI>0,
(ii) CC=(CIR*(TBG−BBG))/IS when BBG<TBG, and the RI is substantially negligible, and
(iii) CC=CIR*(RI+((TBG−BBG)/IS)) when BBG>TBG and RI>(BBG−TBG)/IS, and
(b) a correction bolus (CB) administered in the patient's body, based upon (i) the comparison of the BBG level against the TBG level and (ii) the determined therapeutic course of action, with the correction bolus (CB) calculated by the processor in the following ways:
(i) CB=(BBG−TBG)/IS when BBG>TBG and there is substantially no RI, and
(ii) CB=(BBG−TBG)/IS−RI when BBG>TBG and (BBG−TBG)/IS>RI.

13. The device of claim 12, wherein the therapeutic course of action further includes a patient selected amount of carbohydrates which is less than the calculated amount of carbohydrates (CC) and one of:
an adjustment to the BR to a modified basal rate (BR'), and
advice to the patient to adjust the BR to the BR'.

14. The device of claim 13, wherein if the BBG is less than the TBG and the patient's basal rate (BR) is substantially constant and the RI is substantially negligible, then for any number (n), the therapeutic course of action includes an adjustment of the BR for a time segment (t)=n/BR to the modified basal rate (BR'), wherein the BR'=(IS'/IS)*BR, wherein IS' is a temporal IS value of the patient, n is a positive integer number, and wherein IS'=IS−(TBG−BBG)/n.

15. The device of claim 13, wherein if BBG<TBG and RI >0 and the patient's basal rate (BR) is substantially constant, the therapeutic course of action includes an adjustment of the BR for a time segment (t)=n/BR to the modified basal rate (BR');

wherein IS' is a temporal IS value of the patient, $BG_{ed}$ is an expected decrease in BG, and n is a positive number;
wherein BR'=(IS'/IS)*BR;
wherein IS'=IS−((TBG−(BBG−$BG_{ed}$)/n); and,
wherein $BG_{ed}$=IS*RI.

16. The device of claim 13, wherein if the patient's basal rate (BR) is substantially inconstant, the therapeutic course of action includes the processor adjusting the BR to the modified basal rate (BR').

17. The device of claim 13, wherein if ((BBG<TBG and RI>0) or (BBG>TBG and RI>CB)) and the patient's basal rate (BR) substantially changes over time, the therapeutic course of action includes the processor adjusting the BR to the modified basal rate (BR'), wherein $$IS'_y = IS - \frac{\Delta}{n_y} - \frac{BG_{ed}}{n_y} + \frac{\sum_{x=1}^{x=y-1} IS * n_x}{n_y} - \frac{\sum_{x=1}^{x=y-1} IS * n_{min,x}}{n_y};$$

$y = 1, 2, 3...$ wherein:
 $t_y$ is a period of time in which BR is substantially constant;
 $t_x$ is another period of time;
 n is a positive integer number;
 $n_y$ is an amount of insulin (in units) that is administered during the period of time $t_y$;
 $n_x$ is an amount of insulin (in units) that is administered during the period of time $t_x$;
 $n_{min,x}$ is an amount of insulin (in units) that is administered during the period of time $t_x$ with a minimal possible basal rate;
 IS is an overall decrease in blood glucose;
 IS'y is a temporal IS value during the period of time $t_y$;
 BG is a blood glucose;
 $BG_{ed}$ is an expected decrease in BG;
 $BR_x$ is a basal rate during the period of time $t_x$;
 BR' is the modified basal rate; and
wherein:

$\Delta = TBG - BBG$;

$n_y = t_y * BR'$;

-continued $n_x = t_x * BR_x$;

$n_{min,x} = t_x * BR_{min}$ ($BR_{min}$ = minimal possible basal rate);

$BG_{ed} = IS * RI$, and $BR' = \frac{IS'_y}{IS} * BR.$

18. The device according to claim 17 wherein if a time segment ($t_1$) is longer than a predefined time segment (T), then the adjustment is limited to T according to the following:
 a. $n_1$=T*BRc, wherein BRc is a basal rate at a constant time segment;
 b. IS'$_1$=IS−Δ/$n_1$−RI*IS/$n_1$;
 c. If IS'$_1$>0 then BR'$_1$=(IS'$_1$/IS) * BR for the time segment (T);
 wherein:
  $n_1$ is an amount of insulin (in units) that is administered in the time segment $t_1$;
  IS'$_1$ is an overall decrease in blood glucose in the time segment $t_1$; and
  BR'$_1$ is a modified (adjusted) basal rate for the time segment $t_1$.

19. The device of claim 12, wherein the fasting time period corresponds to a nocturnal time period.

20. The device of claim 12, further comprising a remotely controlled skin adherable unit.

21. The device of claim 20, wherein the remotely controlled skin adherable unit is controllable by one or more bolus buttons and is connectable to and disconnectable from the patient's body.

22. The device of claim 12, wherein the adjustment of the patient's basal rate is reducing the patient's basal rate.

23. The device of claim 12, wherein the device is an insulin infusion pump unit.

24. The device of claim 12, wherein the device is a remote control unit to a patch unit within an insulin infusion device, the insulin infusion device has the patch unit and the remote control unit communicates with the patch unit.

25. The device of claim 12, wherein the device is a glucose measurement unit.

* * * * *

UNITED STATES PATENT AND TRADEMARK OFFICE
CERTIFICATE OF CORRECTION

| | | |
|---|---|---|
| PATENT NO. | : 10,350,354 B2 | Page 1 of 1 |
| APPLICATION NO. | : 12/143611 | |
| DATED | : July 16, 2019 | |
| INVENTOR(S) | : Ofer Yodfat, Gali Shapira and Neesha Ramchandani | |

It is certified that error appears in the above-identified patent and that said Letters Patent is hereby corrected as shown below:

On the Title Page

Item (54), title, delete "Device and method for preventing hypoglicemia" and insert --Device and method for preventing hypoglycemia--, therefor.

In the Specification

In Column 1, Line(s) 1 & 2, delete "Device and method for preventing hypoglicemia" and insert --Device and method for preventing hypoglycemia--, therefor.

In Column 8, Line 38, delete "b. A=TBG-BBG;" and insert --b. Δ=TBG-BBG;--, therefor.

Signed and Sealed this
Third Day of March, 2020

Andrei Iancu
*Director of the United States Patent and Trademark Office*